(12) United States Patent
Robinson et al.

(10) Patent No.: US 9,789,210 B1
(45) Date of Patent: Oct. 17, 2017

(54) METHODS FOR MAKING ULTRASOUND CONTRAST AGENTS

(71) Applicant: Lantheus Medical Imaging, Inc., North Billerica, MA (US)

(72) Inventors: Simon P. Robinson, Stow, MA (US); Robert W. Siegler, Chelmsford, MA (US); Nhung Tuyet Nguyen, Westford, MA (US); David C. Onthank, Groton, MA (US); Tarakeshwar Vishwanath Anklekar, Billerica, MA (US); Charles Chester Van Kirk, Beverly, MA (US)

(73) Assignee: Lantheus Medical Imaging, Inc., North Billerica, MA (US)

( * ) Notice: Subject to any disclaimer, the term of this patent is extended or adjusted under 35 U.S.C. 154(b) by 0 days.

(21) Appl. No.: 15/461,469

(22) Filed: Mar. 16, 2017

Related U.S. Application Data

(60) Provisional application No. 62/359,181, filed on Jul. 6, 2016.

(51) Int. Cl.
*A61B 8/00* (2006.01)
*A61K 49/22* (2006.01)

(52) U.S. Cl.
CPC .......... *A61K 49/223* (2013.01); *A61K 49/227* (2013.01); *A61K 49/22* (2013.01)

(58) Field of Classification Search
None
See application file for complete search history.

(56) References Cited

U.S. PATENT DOCUMENTS

| | | |
|---|---|---|
| 3,873,564 A | 3/1975 | Schneider et al. |
| 4,089,801 A | 5/1978 | Schneider |
| 4,224,179 A | 9/1980 | Schneider |
| 4,229,360 A | 10/1980 | Schneider et al. |
| 5,045,304 A | 9/1991 | Schneider et al. |
| 5,088,499 A | 2/1992 | Unger |
| 5,123,414 A | 6/1992 | Unger |
| 5,149,319 A | 9/1992 | Unger |
| 5,205,290 A | 4/1993 | Unger |
| 5,209,720 A | 5/1993 | Unger |
| 5,228,446 A | 7/1993 | Unger et al. |
| 5,230,882 A | 7/1993 | Unger |
| 5,271,928 A | 12/1993 | Schneider et al. |
| 5,281,408 A | 1/1994 | Unger |
| 5,305,757 A | 4/1994 | Unger et al. |
| 5,334,381 A | 8/1994 | Unger |
| 5,348,016 A | 9/1994 | Unger et al. |
| 5,352,435 A | 10/1994 | Unger |
| 5,358,702 A | 10/1994 | Unger |
| 5,368,840 A | 11/1994 | Unger |
| 5,380,519 A | 1/1995 | Schneider et al. |
| 5,393,524 A | 2/1995 | Quay |
| 5,409,688 A | 4/1995 | Quay |
| 5,413,774 A | 5/1995 | Schneider et al. |
| 5,445,813 A | 8/1995 | Schneider et al. |
| 5,456,900 A | 10/1995 | Unger |
| 5,456,901 A | 10/1995 | Unger |
| 5,469,854 A | 11/1995 | Unger et al. |
| 5,527,521 A | 6/1996 | Unger |
| 5,531,980 A | 7/1996 | Schneider et al. |
| 5,542,935 A | 8/1996 | Unger et al. |
| 5,547,656 A | 8/1996 | Unger |
| 5,558,092 A | 9/1996 | Unger et al. |
| 5,558,094 A | 9/1996 | Quay |
| 5,558,853 A | 9/1996 | Quay |
| 5,558,854 A | 9/1996 | Quay |
| 5,558,855 A | 9/1996 | Quay |
| 5,567,414 A | 10/1996 | Schneider et al. |
| 5,571,497 A | 11/1996 | Unger |
| 5,573,751 A | 11/1996 | Quay |
| 5,578,292 A | 11/1996 | Schneider et al. |
| 5,580,575 A | 12/1996 | Unger et al. |
| 5,585,112 A | 12/1996 | Unger et al. |
| 5,595,723 A | 1/1997 | Quay |
| 5,643,553 A | 7/1997 | Schneider et al. |
| 5,656,211 A | 8/1997 | Unger et al. |
| 5,686,060 A | 11/1997 | Schneider et al. |
| 5,705,187 A | 1/1998 | Unger |
| 5,707,606 A | 1/1998 | Quay |
| 5,707,607 A | 1/1998 | Quay |
| 5,715,824 A | 2/1998 | Unger et al. |
| 5,733,572 A | 3/1998 | Unger et al. |
| 5,736,121 A | 4/1998 | Unger |
| 5,769,080 A | 6/1998 | Unger et al. |
| 5,770,222 A | 6/1998 | Unger et al. |
| 5,773,024 A | 6/1998 | Unger et al. |
| 5,776,429 A | 7/1998 | Unger et al. |
| 5,830,430 A | 11/1998 | Unger et al. |
| 5,846,517 A | 12/1998 | Unger |
| 5,853,752 A | 12/1998 | Unger et al. |

(Continued)

FOREIGN PATENT DOCUMENTS

| | | |
|---|---|---|
| DE | 38 03 972 A1 | 8/1989 |
| EP | 0 052 575 A2 | 5/1982 |

(Continued)

OTHER PUBLICATIONS

Avanti (DPPC) 2017.*
Avanti (DPPE) 2017.*
Avanti (MPEG5000 DPPE) 2017.*
Huntsman (Propylene glycol) 2017.*
Seelig et al. (Biochem. 1984, 23, 3913-3920).*
[No Author Listed], http://www.acusphere.com/product/prod/_imagify.html. In existence as of Apr. 29, 2009.
Chapman, Physicochemical properties of Phospholipids and Lipid-Water Systems. Liposome Technology: Preparation of Liposomes—Chapter 1. Gregory Gregoriadis, Ed. CRC Press, Boca Raton, FL. 1984;1:1-18.
Deamer, Preparation of Solvent Vaporization Liposomes. Liposome Technology: Preparation of Liposomes—Chapter 3. Gregory Gregoriadis, Ed. CRC Press, Boca Raton, FL. 1984;1:29-35.

(Continued)

*Primary Examiner* — Michael G Hartley
*Assistant Examiner* — Melissa J Perreira
(74) *Attorney, Agent, or Firm* — Wolf, Greenfield & Sacks, P.C.

(57) ABSTRACT

Provided herein are improved methods for preparing phospholipid formulations including phospholipid UCA formulations.

9 Claims, 6 Drawing Sheets

(56) References Cited

U.S. PATENT DOCUMENTS

| | | | |
|---|---|---|---|
| 5,874,062 A | 2/1999 | Unger | |
| 5,897,851 A | 4/1999 | Quay et al. | |
| 5,922,304 A | 7/1999 | Unger | |
| 5,935,553 A | 8/1999 | Unger et al. | |
| 5,985,246 A | 11/1999 | Unger | |
| 5,997,898 A | 12/1999 | Unger | |
| 6,001,335 A | 12/1999 | Unger | |
| 6,028,066 A | 2/2000 | Unger | |
| 6,033,645 A | 3/2000 | Unger et al. | |
| 6,033,646 A | 3/2000 | Unger et al. | |
| 6,039,557 A | 3/2000 | Unger et al. | |
| 6,056,938 A | 5/2000 | Unger et al. | |
| 6,071,494 A | 6/2000 | Unger et al. | |
| 6,071,495 A | 6/2000 | Unger et al. | |
| 6,088,613 A | 7/2000 | Unger | |
| 6,090,800 A | 7/2000 | Unger et al. | |
| 6,117,414 A | 9/2000 | Unger | |
| 6,123,923 A | 9/2000 | Unger et al. | |
| 6,139,819 A | 10/2000 | Unger et al. | |
| 6,143,276 A | 11/2000 | Unger | |
| 6,146,657 A | 11/2000 | Unger et al. | |
| 6,214,375 B1 | 4/2001 | Modi | |
| 6,231,834 B1 | 5/2001 | Unger et al. | |
| 6,258,378 B1 | 7/2001 | Schneider et al. | |
| 6,315,981 B1 | 11/2001 | Unger | |
| 6,414,139 B1 | 7/2002 | Unger et al. | |
| 6,416,740 B1 | 7/2002 | Unger | |
| 6,443,898 B1 | 9/2002 | Unger et al. | |
| 6,444,660 B1 | 9/2002 | Unger et al. | |
| 6,461,586 B1 | 10/2002 | Unger | |
| 6,479,034 B1 | 11/2002 | Unger et al. | |
| 6,521,211 B1 | 2/2003 | Unger et al. | |
| 6,528,039 B2 | 3/2003 | Unger | |
| 6,537,246 B1 | 3/2003 | Unger et al. | |
| 6,548,047 B1 | 4/2003 | Unger | |
| 6,551,576 B1 | 4/2003 | Unger et al. | |
| 6,572,840 B1 | 6/2003 | Toler | |
| 6,576,220 B2 | 6/2003 | Unger | |
| 6,716,412 B2 | 4/2004 | Unger | |
| 6,773,696 B2 | 8/2004 | Unger | |
| 6,884,407 B1 | 4/2005 | Unger | |
| 6,943,692 B2 | 9/2005 | Castner et al. | |
| 6,998,107 B2 | 2/2006 | Unger | |
| 7,344,705 B2 | 3/2008 | Unger | |
| 8,084,056 B2 | 12/2011 | Hui et al. | |
| 8,658,205 B2 | 2/2014 | Hui et al. | |
| 8,685,441 B2 | 4/2014 | Hui et al. | |
| 8,747,892 B2 | 6/2014 | Hui et al. | |
| 9,545,457 B2 | 1/2017 | Hui et al. | |
| 2003/0044354 A1 | 3/2003 | Carpenter, Jr. et al. | |
| 2004/0057991 A1 | 3/2004 | Hui et al. | |
| 2005/0163716 A1 | 7/2005 | Unger et al. | |
| 2007/0071685 A1 | 3/2007 | Schneider et al. | |
| 2008/0009561 A1 | 1/2008 | Unger et al. | |
| 2008/0118435 A1 | 5/2008 | Unger | |
| 2012/0027688 A1 | 2/2012 | Hui et al. | |
| 2012/0128595 A1 | 5/2012 | Hui et al. | |
| 2013/0022550 A1 | 1/2013 | Unger et al. | |
| 2013/0123781 A1 | 5/2013 | Grubbs et al. | |
| 2013/0309175 A1 | 11/2013 | Hui et al. | |
| 2016/0000943 A1 | 1/2016 | Unger et al. | |
| 2016/0331851 A1 | 11/2016 | Robinson et al. | |

FOREIGN PATENT DOCUMENTS

| | | |
|---|---|---|
| EP | 0 077 752 A2 | 4/1983 |
| EP | 0 224 934 A2 | 6/1987 |
| EP | 0 231 091 A1 | 8/1987 |
| EP | 0 274 961 A1 | 7/1988 |
| EP | 0 314 764 A1 | 5/1989 |
| EP | 0 324 938 A1 | 7/1989 |
| EP | 0 338 971 A1 | 10/1989 |
| EP | 0 349 429 A2 | 1/1990 |
| EP | 0 458 745 A1 | 11/1991 |
| EP | 0 554 213 A1 | 8/1993 |
| EP | 0 901 793 A1 | 3/1999 |
| EP | 0 957 942 A2 | 11/1999 |
| JP | 63-60943 | 3/1988 |
| JP | 63-277618 A | 11/1988 |
| JP | 2-149336 A | 6/1990 |
| JP | 8-151335 A | 6/1996 |
| WO | WO 80/02365 A1 | 11/1980 |
| WO | WO 82/01642 A1 | 5/1982 |
| WO | WO 85/02772 A1 | 7/1985 |
| WO | WO 89/10118 A1 | 11/1989 |
| WO | WO 90/04384 A1 | 5/1990 |
| WO | WO 90/14846 A1 | 12/1990 |
| WO | WO 91/00086 A1 | 1/1991 |
| WO | WO 91/09629 A1 | 7/1991 |
| WO | WO 91/15244 A2 | 10/1991 |
| WO | WO 91/15753 A1 | 10/1991 |
| WO | WO 92/10166 A1 | 6/1992 |
| WO | WO 92/15284 A1 | 9/1992 |
| WO | WO 92/17212 A1 | 10/1992 |
| WO | WO 92/17514 A1 | 10/1992 |
| WO | WO 92/22247 A1 | 12/1992 |
| WO | WO 92/22249 A1 | 12/1992 |
| WO | WO 92/22298 A1 | 12/1992 |
| WO | WO 93/05819 A1 | 4/1993 |
| WO | WO 93/06869 A1 | 4/1993 |
| WO | WO 93/13802 A1 | 7/1993 |
| WO | WO 94/09829 A1 | 5/1994 |
| WO | WO 94/16739 A1 | 8/1994 |
| WO | WO 94/21301 A1 | 9/1994 |
| WO | WO 94/21302 A1 | 9/1994 |
| WO | WO 94/28780 A2 | 12/1994 |
| WO | WO 94/28797 A1 | 12/1994 |
| WO | WO 94/28873 A1 | 12/1994 |
| WO | WO 94/28874 A1 | 12/1994 |
| WO | WO 95/03835 A1 | 2/1995 |
| WO | WO 95/06518 A1 | 3/1995 |
| WO | WO 95/07072 A2 | 3/1995 |
| WO | WO 95/12387 A2 | 5/1995 |
| WO | WO 95/15118 A1 | 6/1995 |
| WO | WO 95/16467 A1 | 6/1995 |
| WO | WO 95/23615 A1 | 9/1995 |
| WO | WO 95/24184 A1 | 9/1995 |
| WO | WO 95/26205 A1 | 10/1995 |
| WO | WO 95/32005 A1 | 11/1995 |
| WO | WO 95/32006 A1 | 11/1995 |
| WO | WO 96/04018 A1 | 2/1996 |
| WO | WO 96/08234 A1 | 3/1996 |
| WO | WO 96/09793 A1 | 4/1996 |
| WO | WO 96/31196 A1 | 10/1996 |
| WO | WO 96/40281 A2 | 12/1996 |
| WO | WO 96/40285 A1 | 12/1996 |
| WO | WO 97/00638 A2 | 1/1997 |
| WO | WO 97/40679 A1 | 11/1997 |
| WO | WO 97/40858 A1 | 11/1997 |
| WO | WO 97/48337 A1 | 12/1997 |
| WO | WO 98/04292 A2 | 2/1998 |
| WO | WO 98/10798 A1 | 3/1998 |
| WO | WO 98/10799 A1 | 3/1998 |
| WO | WO 98/17324 A2 | 4/1998 |
| WO | WO 98/18495 A2 | 5/1998 |
| WO | WO 98/18498 A2 | 5/1998 |
| WO | WO 98/18500 A2 | 5/1998 |
| WO | WO 98/18501 A2 | 5/1998 |
| WO | WO 98/42384 A1 | 10/1998 |
| WO | WO 98/51284 A1 | 11/1998 |
| WO | WO 99/08714 A1 | 2/1999 |
| WO | WO 99/13919 A1 | 3/1999 |
| WO | WO 99/30620 A1 | 6/1999 |
| WO | WO 99/36104 A2 | 7/1999 |
| WO | WO 99/39738 A1 | 8/1999 |
| WO | WO 00/45856 A2 | 8/2000 |
| WO | WO 2004/030617 A1 | 4/2004 |

OTHER PUBLICATIONS

Lelkes, The Use of French Pressed Vesicles for Efficient Incorporation of Bioactive Macromolecules and as Drug Carriers In Vitro and In Vivo. Liposome Technology: Preparation of Liposomes—

(56) References Cited

OTHER PUBLICATIONS

Chapter 5. Gregory Gregoriadis, Ed. CRC Press, Boca Raton, FL. 1984;1:51-65.
Weder et al., The Preparation of Variably Sized Homogeneous Liposomes for Laboratory, Clinical, and Industrial Use by Controlled Detergent Dialysis. Liposome Technology: Preparation of Liposomes—Chapter 7. Gregory Gregoriadis, Ed. CRC Press, Boca Raton, FL. 1984;1:79-107.
[No Author Listed] Division of new drug chemistry document relating to Definity. Review date, Feb. 15, 2001.
[No Author Listed] EMEA Scientific discussion relating to Sonovue. Updated until Oct. 1, 2004. 1 page.
[No Author Listed] http://www.acusphere.com/product/prod/_imagify.html, 2009.
[No Author Listed] Definity FDA Approval Label. Initial US Approval: 2001. U.S. Food and Drug Administration. Silver Spring, Maryland. Revised Aug. 2015, 19 pages.
Bedu-Addo, F.K., et al., "Effects of polyethyleneglycol chain length and phospholipids acyl chain composition on the interaction of polyethyleneglycol-phospholipid conjugants with phospholipids: implications in liposomal drug delivery," Pharm. Res., May 1996, 13(5), 710-717.
Belsito, S., et al., "Sterically stabilized liposomes of DPPC/DPPE-PEG 2000—A spin label ESR & spectrophotometric study," Biophysical Chem., May 10, 1998, 75(1), 33-43.
Blomley et al., "Microbubble contrast agents: a new era in ultrasound"; Clinical Review XP008001399, BMJ, vol. 322, pp. 1222-1225 (May 19, 2001).
De Jong et al., New ultrasound contrast agents and technological innovations. Ultrasonics. Jun. 1996;34(2-5):587-90.
Feinstein et al., "Two-Dimensional Contrast Echocardiography. I. In Vitro Development and Quantitative Analysis of Echo Contrast Agents", JACC, vol. 3, No. 1, pp. 14-20 (1984).
Fritzsch et al., "Preclinical and Clinical Results with an Ultrasonic Contrast Agent", Inv. Rad., vol. 23, pp. S302-S305, Sep. 1988.
Gabizon et al., "Liposome formulations with prolonged circulation time in blood and enhanced uptake by tumors", Proc. Natl. Acad. Sci., vol. 85, pp. 6949-6953 (1988).
Goldberg, et al., "Ultrasound contrast agents: a review," Ultrasound in Med. & Biol., 1994, 20(4), 319-333.
Gregodiadis, G., et al. (Eds.), "Liposome technology: preparation of liposomes," and Deamer: "Preparation of solvent vaporization liposomes,"CRC Press, Inc., 1984, CRC Press, Inc., XP002101586, vol. 1, 30-35, 51-65, 79-107.
Gross, U. et al., "Phospholipid vesiculated fluorocarbons promising trend in blood substitutes" Biomat., Art. Cells & Immob. Biotech., 1992, vol. 20, (2-4) pp. 831-833.
Hettiarachchi et al., On-chip generation of microbubbles as a practical technology for manufacturing contrast agents for ultrasonic imaging. Lab Chip. Apr. 2007;7(4):463-8. Epub Mar. 8, 2007.
Hope et al., "Generation of Multilamellar and Unilamellar Phospholipid Vesicles", Chemistry and Physics of Lipids, vol. 40, pp. 89-107 (1986).
Ishida et al., Accelerated clearance of PEGylated liposomes in rats after repeated injections. J Control Release. Feb. 14, 2003;88(1):35-42.
Kitzman et al., Efficacy and safety of the novel ultrasound contrast agent perflutren (Definity) in patients with suboptimal baseline left ventricular echocardiographic images. Am J Cardiol. Sep. 15, 2000;86(6):669-74.
Nikolova, A., et al., "Effect of grafted PEG-2000 on the size and permeability of vesicles," Biochim Biophys Acta, Nov. 22, 1996, 1304(2), 120-128.
Ohki, et al., "Short & long range calcium-induced lateral phase separations in ternary mixtures of phosphatidic acid phosphatidylcholine and phosphatidylethanolamine," Chem. & Physics of Lipids, 1989, 50(2), 109-118.
Ophir et al., "Contrast Agents in Diagnostic Ultrasound", Ultrasound in Med. & Biol., vol. 15, No. 4, pp. 319-333 (1989).

Sarkar et al., Growth and dissolution of an encapsulated contrast microbubble: effects of encapsulation permeability. Ultrasound Med Biol. Aug. 2009;35(8):1385-96. doi: 10.1016/j.ultrasmedbio.2009.04.010.
Schutt et al., "Osmotically Stabilized Microbubble Sonographic Contrast Agents", Acad. Radiol., vol. 3, Suppl. 2, pp. S188-S190 (Aug. 1996).
Senior et al., Investigators. Detection of coronary artery disease with perfusion stress echocardiography using a novel ultrasound imaging agent: two Phase 3 international trials in comparison with radionuclide perfusion imaging. Eur J Echocardiogr. Jan. 2009;10(1):26-35.
Senior, Imagify (perflubutane polymer microspheres) injectable suspension for the assessment of coronary artery disease. Expert Rev Cardiovasc Ther. May 2007;5(3):413-21.
Swanson et al., "Enhancement Agents for Ultrasound: Fundamentals", Pharmaceuticals in Medical Imaging, Chapter 22, pp. 682-687 (1990).
Szoka, et al., "Comparative properties and methods of preparation of liqid vesicles (Liposomes)," Ann. Rev. Biophys. Bioeng., 1980,9, 467-508.
Unger et al., "Gas filled lipid bilayers as imaging contrast agents," J. Liposome Res., 1994, 4(2), 861-874.
Unger et al., "Gas-filled lipid bilayers as ultrasound contrast agent," Invest. Radiol., 1994, 29S2, S134-S136.
Unger et al., "In Vitro Studies of a New Thrombus-Specific Ultrasound Contrast Agent", American Journal of Cardiology, vol. 81, No. 12, Suppl. A, pp. 58G-61G, XP-002087505, Jun. 12, 1998 and Symposium: Ninth International Congress on Echocardiography: Clinical Cardiology, 1997.
Unger et al., "Liposomal MR Contrast Agents", J. Liposome Research, 4(2), pp. 811-834 (1994).
Unger et al., "Hepatic Metastases: Liposomal Gd-DTPA-enhanced MR Imaging", Radiology, vol. 171, No. 1, pp. 81-85 (1989).
Wang et al., Anti-PEG IgM elicited by injection of liposomes is involved in the enhanced blood clearance of a subsequent dose of PEGylated liposomes. J Control Release. Jun. 4, 2007;119(2):236-44. Epub Feb. 24, 2007.
Yuda et al., Prolongation of liposome circulation time by various derivatives of polyethyleneglycols. Biol Pharm Bull. Oct. 1996;19(10):1347-51.
Ali et al., Speciation of Metal Ions by Reversed-Phase High-Performance Liquid Chromatography. Instrumental Methods in Metal Ion Speciation—Chapter 6. CRC Press. Taylor and Francis Group, LLC. 2006:163-93.
Clabaugh et al., Separation and Determination of Phosphate, Silicate, and Arsenate. Journal of Research of the National Bureau of Standards. May 1959;62(5):201-5.
Ellingson et al., Phospholipid reactivation of plasmalogen metabolism. Lipids. Mar. 1968;3(2):111-20.
Mangold, Thin-Layer Chromatography of Lipids. J. Am. Oil Chemists' Soc. Dec. 1961;38:708-27.
Sims et al., The Use of Iodine as a General Detecting Agent in the Thin Layer Chromatography of Lipids. J. Am. Oil Chemists' Soc. Jan. 1962;39:232.
Skipski et al., Separation of phosphatidyl ethanolamine, phosphatidyl derine, and other phospholipids by thin-layer chromatography. J. Lipid Research. Oct. 1962;3(4):467-70.
Avanti Polar Lipids Product Sheet for MPEG5000-DPPE (16:0 PEG5000 PE), Product No. 880200; Downloaded from www.avantilipids.com on Aug. 21, 2017; 2 pages.
Avanti Polar Lipids Research Certificate of Analysis for MPEG5000-DPPE (16:0 PEG5000 PE), Product No. 880200P, Lot 160PEG5PE-56; Downloaded from www.avantilipids.com on Aug. 21, 2017; 1 page.
Avanti Polar Lipids Description for Thin Layer Chromatography (TLC) Analysis of Phospholipids; Downloaded from www.avantilipids.com on Aug. 21, 2017; 2 pages.
Avanti Polar Lipids Description for Detection Methods for Thin Layer Chromatography (TLC): Detection of Phosphorus and Detection of Amines; Downloaded from www.avantilipids.com on Aug. 21, 2017; 3 pages.

(56) References Cited

OTHER PUBLICATIONS

Avanti Polar Lipids Description for HPLC Separation of Phospholipids; Downloaded from www.avantilipids.com on Aug. 21, 2017; 3 pages.
Avanti Polar Lipids Description for Fatty Acid Analysis of Phospholipids by GC/FID (GC-FAME Assay); Downloaded from www.avantilipids.com on Aug. 21, 2017; 2 pages.
Pending U.S. Appl. No. 15/374,147, filed Dec. 9, 2016.
Pending U.S. Appl. No. 15/523,031, filed Apr. 28, 2017.
Pending U.S. Appl. No. 15/602,534, filed May 23, 2017.
Pending U.S. Appl. No. 15/587,368, filed May 4, 2017.
Pending U.S. Appl. No. 15/602,580, filed May 23, 2017.

\* cited by examiner

METHODS FOR MAKING ULTRASOUND CONTRAST AGENTS

RELATED APPLICATIONS

This application claims the benefit under 35 U.S.C. §119 (e) of U.S. provisional application No. 62/359,181, filed Jul. 6, 2016, which is incorporated by reference herein in its entirety.

BACKGROUND

Lipid-encapsulated gas microspheres are used as contrast agents in ultrasound imaging applications.

SUMMARY

The disclosure provides improved methods for preparing phospholipid-based ultrasound contrast agents. The disclosure is based in part on the unexpected finding that certain phospholipid-based ultrasound contrast agent formulations are susceptible to divalent metal cations. In the presence of particular levels of certain of those cations, phospholipids and potentially other components in the formulation precipitate rendering the formulation unusable. It was not heretofore appreciated that certain divalent metal cations had the ability to so negatively impact the ultrasound contrast agent formulation.

Based on these findings, this disclosure contemplates improved methods for synthesizing such formulations that prevent such unwanted phospholipid precipitation as well as the formulations resulting from such methods. Also provided are methods for using these improved formulations in the synthesis of improved ultrasound contrast agents, and their use in imaging subjects in need thereof.

Thus, in one aspect, provided herein is a method for preparing a phospholipid suspension, comprising providing DPPA, DPPC and MPEG5000-DPPE stocks, measuring calcium concentration of one or more or all of the DPPC, DPPA and MPEG5000-DPPE stocks, combining the DPPA, DPPC and/or MPEG5000-DPPE stocks with a non-aqueous solvent to form a phospholipid solution, and combining the phospholipid solution with an aqueous solvent to form a phospholipid suspension. In some embodiments, the method further comprises measuring calcium concentration of the non-aqueous solvent.

In some embodiments, the combined measured calcium concentration of the DPPA, DPPC and/or MPEG5000-DPPE stocks is low (i.e., the sum of or the combined calcium concentration for the measured stocks, whether such measured stocks are DPPA alone, DPPC alone, MPEG5000-DPPE alone, DPPA and DPPC, DPPA and MPEG5000-DPPE, DPPC and MPEG5000-DPPE, or DPPA, DPPC and MPEG5000-DPPE, is low).

In some embodiments, the combined measured calcium concentration of the DPPA, DPPC and/or MPEG-DPPE stocks and the non-aqueous solvent is low (i.e., the sum of or the combined calcium concentration for the measured components, whether such measured components are DPPA alone or DPPA and non-aqueous solvent, DPPC alone or DPPA and non-aqueous solvent, MPEG5000-DPPE alone or MPEG5000-DPPE and non-aqueous solvent, DPPA and DPPC or DPPA, DPPC and non-aqueous solvent, DPPA and MPEG5000-DPPE or DPPA, MPEG5000-DPPE and non-aqueous solvent, DPPC and MPEG5000-DPPE or DPPC, MPEG5000-DPPE and non-aqueous solvent, DPPA, DPPC and MPEG5000-DPPE or DPPA, DPPC, MPEG5000-DPPE and non-aqueous solvent, is low).

In some embodiments, the calcium concentrations of the DPPC, DPPA and MPEG5000-DPPE stocks are measured.

In some embodiments, the calcium concentrations of the DPPC, DPPA and MPEG5000-DPPE stocks are measured and the combined measured calcium concentration of the DPPA, DPPC, MPEG-DPPE stocks and the non-aqueous solvent is low.

Thus, depending on the embodiment, only the calcium concentration of DPPA is measured, or only the calcium concentration of DPPC is measured, or only the calcium concentration of MPEG5000-DPPE is measured, or only the calcium concentrations of DPPA and DPPC are measured (and such concentrations are added together to yield a combined measured calcium concentration), or only the calcium concentrations of DPPA and MPEG5000-DPPE are measured (and such concentrations are added together to yield a combined measured calcium concentration), or only the calcium concentrations of DPPC and MPEG5000-DPPE are measured (and such concentrations are added together to yield a combined measured calcium concentration), or only the calcium concentrations of DPPA, DPPC and MPEG5000-DPPE are measured (and such concentrations are added together to yield a combined measured calcium concentration), or only the calcium concentrations of DPPA and non-aqueous solvent are measured (and such concentrations are added together to yield a combined measured calcium concentration), or only the calcium concentrations of DPPC and non-aqueous solvent are measured (and such concentrations are added together to yield a combined measured calcium concentration), or only the calcium concentrations of MPEG5000-DPPE and non-aqueous solvent are measured (and such concentrations are added together to yield a combined measured calcium concentration), or only the calcium concentrations of DPPA, DPPC and non-aqueous solvent are measured (and such concentrations are added together to yield a combined measured calcium concentration), or only the calcium concentrations of DPPA, MPEG5000-DPPE and non-aqueous solvent are measured (and such concentrations are added together to yield a combined measured calcium concentration), or only the calcium concentrations of DPPC, MPEG5000-DPPE and non-aqueous solvent are measured (and such concentrations are added together to yield a combined measured calcium concentration), or the calcium concentrations of DPPA, DPPC, MPEG5000-DPPE and non-aqueous solvent are measured (and such concentrations are added together to yield a combined measured calcium concentration). It should be clear that every combination of components is contemplated in arriving at a combined measured or characterized (as discussed below) calcium concentration. It is to be understood that the terms DPPA, DPPA lipid, DPPA phospholipid, DPPA stock, DPPA lipid stock, and DPPA phospholipid stock are used interchangeably unless explicitly stated otherwise. Similar interchangeable terms are used for DPPC and MPEG5000-DPPE.

This disclosure further provides in another aspect a method for preparing a phospholipid suspension, comprising providing DPPA, DPPC and MPEG5000-DPPE stocks, measuring calcium concentration of one or more or all of the DPPC, DPPA and MPEG5000-DPPE stocks, combining DPPA, DPPC and/or MPEG5000-DPPE stocks having a combined measured low calcium concentration with a non-aqueous solvent to form a phospholipid solution, and combining the phospholipid solution with an aqueous solvent to form a phospholipid suspension. In some embodiments, the method further comprises measuring the calcium concentration of the non-aqueous solvent and the DPPA, DPPC, MPEG500-DPPE stocks and the non-aqueous solvent have a combined measured low calcium concentration.

This disclosure further provides in another aspect a method for preparing a phospholipid suspension, comprising combining a MPEG5000-DPPE stock, a DPPA stock, a DPPC stock and a non-aqueous solvent, each with characterized calcium concentration to form a phospholipid solution, wherein the combined characterized calcium concentration of the MPEG5000-DPPE stock, the DPPA stock, the DPPC stock and the non-aqueous solvent is a low calcium concentration, and combining the phospholipid solution with an aqueous solvent to form a phospholipid suspension This disclosure further provides in another aspect a method for preparing a phospholipid suspension, comprising selecting a MPEG5000-DPPE stock, a DPPA stock and a DPPC stock, one, two or all three of which have a characterized calcium concentration, wherein the combined characterized calcium concentration is a low calcium concentration, combining said MPEG5000-DPPE stock, DPPA stock, DPPC stock and a non-aqueous solvent to form a phospholipid solution, and combining the phospholipid solution with an aqueous solvent to form a phospholipid suspension. Components such as phospholipid stocks and/or non-aqueous solvent are so selected on the basis of having an individual or a combined characterized calcium concentration.

This disclosure further provides in another aspect a method for preparing a phospholipid suspension, comprising selecting a MPEG5000-DPPE stock, a DPPA stock and a DPPC stock, each with characterized calcium concentration, wherein the combined characterized calcium concentration is a low calcium concentration, combining said MPEG5000-DPPE stock, DPPA stock, DPPC stock and a non-aqueous solvent to form a phospholipid solution, and combining the phospholipid solution with an aqueous solvent to form a phospholipid suspension. In some embodiments, the non-aqueous solvent has a characterized calcium concentration, and the combined characterized calcium concentration of the MPEG5000-DPPE, DPPA and DPPC stocks and the non-aqueous solvent is low.

This disclosure further provides in another aspect a method for preparing a phospholipid suspension, comprising measuring calcium concentration of a MPEG5000-DPPE stock, combining a MPEG5000-DPPE stock having a measured low calcium concentration with a DPPA stock, a DPPC stock, and a non-aqueous solvent to form a phospholipid solution, and combining the phospholipid solution with an aqueous solvent to form a phospholipid suspension. In some embodiments, the low calcium concentration is less than 115 ppm.

This disclosure further provides in another aspect a method for preparing a phospholipid suspension comprising measuring calcium concentration of a DPPC stock, combining a DPPC stock having a measured low calcium concentration with a DPPA stock, a MPEG5000-DPPE stock, and a non-aqueous solvent to form a phospholipid solution, and combining the phospholipid solution with an aqueous solvent to form a phospholipid suspension. In some embodiments, the low calcium concentration is less than 90 ppm.

This disclosure further provides in another aspect a method for preparing a phospholipid suspension comprising measuring calcium concentration of a DPPA stock, combining a DPPA stock having a measured low calcium concentration with a DPPC stock, a MPEG5000-DPPE stock, and a non-aqueous solvent to form a phospholipid solution, and combining the phospholipid solution with an aqueous solvent to form a phospholipid suspension. In some embodiments, the low calcium concentration is less than 780 ppm.

This disclosure further provides in another aspect a method for preparing a phospholipid suspension comprising measuring calcium concentration of a non-aqueous solvent, combining a non-aqueous solvent having a measured low calcium concentration with a DPPA stock, a DPPC stock, and a MPEG5000-DPPE stock, to form a phospholipid solution, and combining the phospholipid solution with an aqueous solvent to form a phospholipid suspension. In some embodiments, the low calcium concentration is less than 0.7 ppm.

This disclosure further provides in another aspect a method for preparing a phospholipid suspension comprising combining MPEG5000-DPPE, DPPA and DPPC stocks with a non-aqueous solvent to form a phospholipid solution, measuring calcium concentration of the phospholipid solution, and combining a phospholipid solution having a measured low calcium concentration with an aqueous solvent to form a phospholipid suspension.

This disclosure further provides in another aspect a method for preparing a phospholipid suspension, comprising selecting a MPEG5000-DPPE stock characterized as having no or low calcium concentration, combining said MPEG5000-DPPE stock, a DPPA stock, a DPPC stock and a non-aqueous solvent to form a phospholipid solution, and combining the phospholipid solution with an aqueous solvent to form a phospholipid suspension. In some embodiments, the MPEG5000-DPPE stock is further characterized as having no or low divalent metal cation content.

This disclosure further provides in another aspect a method for preparing a phospholipid suspension, comprising combining a MPEG5000-DPPE stock, a DPPA stock, a DPPC stock and a non-aqueous solvent to form a phospholipid solution characterized as having no or low calcium concentration, and combining the phospholipid solution with an aqueous solvent to form a phospholipid suspension.

This disclosure further provides in another aspect a method for imaging a subject comprising combining a phospholipid suspension with a perfluorocarbon gas to form an ultrasound contrast agent comprising phospholipid-encapsulated gas microspheres, administering the ultrasound contrast agent to a subject, and obtaining one or more contrast-enhanced ultrasound contrast images of the subject, wherein the phospholipid suspension is prepared by any of the foregoing methods.

This disclosure further provides in another aspect a method for imaging a subject comprising combining a phospholipid suspension with a perfluorocarbon gas to form an ultrasound contrast agent comprising phospholipid-encapsulated gas microspheres, administering the ultrasound contrast agent to a subject, and obtaining one or more contrast-enhanced ultrasound contrast images of the subject, wherein the phospholipid suspension is prepared by a method comprising measuring calcium concentration of MPEG5000-DPPE stock, combining a MPEG5000-DPPE stock having a measured low calcium concentration with a DPPA stock, a DPPC stock, and a non-aqueous solvent to form a phospholipid solution, and combining the phospholipid solution with an aqueous solvent to form the phospholipid suspension.

This disclosure further provides in another aspect a method for imaging a subject comprising combining a phospholipid suspension with a perfluorocarbon gas to form an ultrasound contrast agent comprising phospholipid-encapsulated gas microspheres, administering the ultrasound contrast agent to a subject, and obtaining one or more contrast-enhanced ultrasound contrast images of the subject, wherein the phospholipid suspension is prepared by a method comprising combining MPEG5000-DPPE, DPPA and DPPC stocks with a non-aqueous solvent to form a phospholipid solution, measuring calcium concentration of the phospholipid solution, and combining a phospholipid solution having a measured low calcium concentration with an aqueous solvent to form a phospholipid suspension.

This disclosure further provides in another aspect a method for imaging a subject comprising combining a phospholipid suspension with a perfluorocarbon gas to form an ultrasound contrast agent comprising phospholipid-encapsulated gas microspheres, administering the ultrasound contrast agent to a subject, and obtaining one or more contrast-enhanced ultrasound contrast images of the subject, wherein the phospholipid suspension is prepared by a method comprising selecting a MPEG5000-DPPE stock characterized as having no or low calcium concentration, combining said MPEG5000-DPPE stock, a DPPA stock, a DPPC stock and a non-aqueous solvent to form a phospholipid solution, and combining the phospholipid solution with an aqueous solvent to form a phospholipid suspension.

This disclosure further provides in another aspect a method for imaging a subject comprising combining a phospholipid suspension with a perfluorocarbon gas to form an ultrasound contrast agent comprising phospholipid-encapsulated gas microspheres, administering the ultrasound contrast agent to a subject, and obtaining one or more contrast-enhanced ultrasound contrast images of the subject, wherein the phospholipid suspension is prepared by a method comprising combining a MPEG5000-DPPE stock, a DPPA stock, a DPPC stock and a non-aqueous solvent to form a phospholipid solution characterized as having no or low calcium concentration, and combining the phospholipid solution with an aqueous solvent to form a phospholipid suspension.

This disclosure further provides in another aspect a method for preparing a phospholipid suspension, comprising individually combining DPPA, DPPC and MPEG5000-DPPE stocks with a PG-comprising non-aqueous solvent, in a low or no calcium condition, to form a phospholipid solution, and combining the phospholipid solution with an aqueous solvent to form a phospholipid suspension. In some embodiments, the no or low calcium condition is less than 0.7 ppm.

This disclosure further provides in another aspect a method for preparing a phospholipid suspension, comprising sequentially combining DPPA, DPPC and MPEG5000-DPPE stocks with a PG-comprising non-aqueous solvent, in a low or no calcium condition, in an order-independent manner, to form a phospholipid solution, and combining the phospholipid solution with an aqueous solvent to form a phospholipid suspension. In some embodiments, the no or low calcium condition is less than 0.7 ppm.

This disclosure further provides in another aspect a method for preparing a phospholipid suspension, comprising combining, in a methanol and toluene-free condition, DPPA, DPPC and MPEG5000-DPPE stocks to form a phospholipid blend, combining the phospholipid blend with a PG-comprising non-aqueous solvent, in a low or no calcium condition, to form a phospholipid solution, and combining the phospholipid solution with an aqueous solvent to form a phospholipid suspension. In some embodiments, the no or low calcium condition is less than 0.7 ppm.

This disclosure further provides in another aspect a method for preparing a phospholipid suspension, comprising combining DPPA, DPPC and MPEG5000-DPPE stocks with a blend solvent to form a phospholipid blend, evaporating the blend solvent to form a dried phospholipid blend, combining the dried phospholipid blend with a PG-comprising non-aqueous solvent, in a low or no calcium condition, to form a phospholipid solution, and combining the phospholipid solution with an aqueous solvent to form a phospholipid suspension. In some embodiments, the no or low calcium condition is less than 0.7 ppm.

This disclosure further provides in another aspect a method for preparing a phospholipid suspension, comprising combining DPPA, DPPC and MPEG5000-DPPE stocks with a blend solvent to form a phospholipid blend, precipitating, in a MTBE-free condition, the phospholipid blend using a second blend solvent, combining the precipitated phospholipid blend with a non-aqueous solvent, in a low or no calcium condition, to form a phospholipid solution, and combining the phospholipid solution with an aqueous solvent to form a phospholipid suspension. In some embodiments, the no or low calcium condition is less than 0.7 ppm.

In some embodiments of any of the foregoing methods, the method further comprises combining the phospholipid suspension with a perfluorocarbon gas to form an ultrasound contrast agent comprising phospholipid-encapsulated gas microspheres. In some embodiments of any of the foregoing methods, the method further comprises administering the ultrasound contrast agent to a subject and obtaining one or more contrast-enhanced ultrasound images of the subject.

This disclosure further provides in another aspect a method for imaging a subject comprising combining a phospholipid suspension with a perfluorocarbon gas to form an ultrasound contrast agent comprising phospholipid-encapsulated gas microspheres, administering the ultrasound contrast agent to a subject, and obtaining one or more contrast-enhanced ultrasound contrast images of the subject, wherein the phospholipid suspension is prepared by any one of the foregoing methods.

This disclosure further provides in other aspects a composition comprising a phospholipid solution comprising DPPA, DPPC and MPEG5000-DPPE in a non-aqueous solvent and having a low calcium concentration, as well as a composition comprising a phospholipid solution comprising DPPA, DPPC and MPEG5000-DPPE in a non-aqueous solvent, wherein the DPPA, DPPC and MPEG5000-DPPE and the non-aqueous solvent have a combined characterized calcium ion content that is low. In some embodiments, the non-aqueous solvent comprises propylene glycol (e.g., propylene glycol may be the only non-aqueous solvent or it may be used in combination with one or more other solvents to render a non-aqueous solvent). In some embodiments, the non-aqueous solvent comprises propylene glycol and glycerol. In some embodiments, the non-aqueous solvent comprises a buffer. In some embodiments, the buffer is acetate buffer. In some embodiments, the composition comprises a perfluorocarbon gas. In some embodiments, the perfluorocarbon gas is perflutren. Thus, in some instances, the composition is provided in a container such as a vial, and the gas is provided in the headspace of the container. Also provided are methods for combining the phospholipid solution with the perfluorocarbon gas to form an ultrasound contrast agent comprising phospholipid-encapsulated gas microspheres. The method may further comprise administering the ultrasound contrast agent to a subject and obtaining one or more contrast-enhanced ultrasound images of the subject.

In some embodiments of the various aspects provided herein, the non-aqueous solvent comprises (i) propylene glycol or (ii) propylene glycol and glycerol.

In some embodiments of the various aspects provided herein, the non-aqueous solvent comprises a buffer. In some embodiments of the various aspects provided herein, the non-aqueous solvent comprises an acetate buffer.

In some embodiments of the various aspects provided herein, the aqueous solvent comprises a buffer. In some embodiments of the various aspects provided herein, the aqueous solvent comprises a phosphate buffer.

In some embodiments of the various aspects provided herein, the DPPC, DPPA and MPEG5000-DPPE stocks are individually combined with the non-aqueous solvent to form the phospholipid solution.

In some embodiments of the various aspects provided herein, the DPPC, DPPA and MPEG5000-DPPE stocks are sequentially combined with the non-aqueous solvent, in an order-independent manner, to form the phospholipid solution.

In some embodiments of the various aspects provided herein, the DPPC, DPPA and MPEG5000-DPPE stocks are combined with each other to form a phospholipid mixture and the phospholipid mixture is then combined with the non-aqueous solvent to form the phospholipid solution. The phospholipid mixture may be heterogeneous or homogeneous.

In some embodiments of the various aspects provided herein, the DPPC, DPPA and MPEG5000-DPPE stocks are combined with each other to form a phospholipid blend, and the phospholipid blend is combined with the non-aqueous solvent to form the phospholipid solution. In some embodiments of the various aspects provided herein, the phospholipid blend is formed using an organic solvent dissolution-precipitation process comprising dissolving the DPPC, DPPA and MPEG5000-DPPE stocks into a mixture of methanol and toluene, optionally concentrating the phospholipid/methanol/toluene mixture, and then contacting the concentrated phospholipid/methanol/toluene mixture with methyl t-butyl ether (MTBE) to precipitate the phospholipids to form the phospholipid blend. In some embodiments of the various aspects provided herein, the phospholipid blend is formed by dissolving DPPC, DPPA and MPEG5000-DPPE stocks into a blend solvent system, other than a methanol/toluene solvent system, optionally concentrating the phospholipid/solvent mixture, and then contacting the concentrated phospholipid/solvent mixture with methyl t-butyl ether (MTBE) to precipitate the phospholipids to form the phospholipid blend. In some embodiments of the various aspects provided herein, the phospholipid blend is formed by dissolving DPPC, DPPA and MPEG5000-DPPE stocks into a blend solvent system, such as but not limited to a methanol/toluene solvent system, and then lyophilizing or otherwise drying the mixture to remove the solvent, leaving behind the phospholipid blend.

In some embodiments of the various aspects provided herein, the method further comprises placing the phospholipid suspension in a vial and introducing a perfluorocarbon gas into the headspace of the vial.

In some embodiments of the various aspects provided herein, the method further comprises activating the phospholipid suspension with the perfluorocarbon gas to form an ultrasound contrast agent comprising phospholipid-encapsulated gas microspheres.

In some embodiments of the various aspects provided herein, the method further comprises administering the ultrasound contrast agent to a subject and obtaining one or more contrast-enhanced ultrasound images of the subject.

In some embodiments of the various aspects provided herein, the method further comprises measuring calcium concentration of the DPPA stock and/or DPPC stock and/or phospholipid mixture and/or phospholipid blend.

These and other aspects and embodiments of this disclosure will be described in greater detail herein.

DETAILED DESCRIPTION

Figure 1:
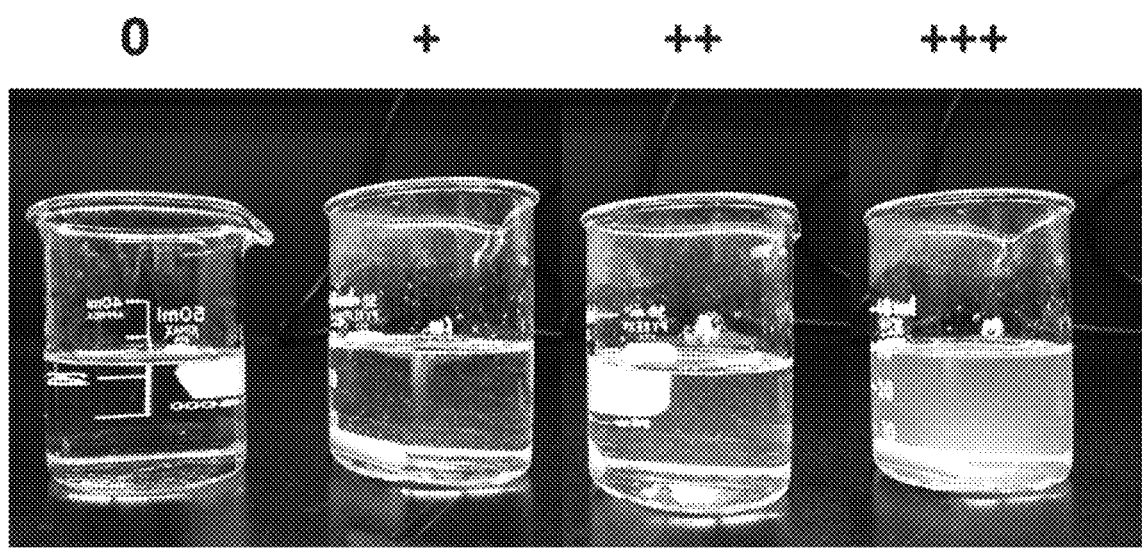
FIG. 1 is a photograph of four phospholipid solutions having differing degrees of precipitation. The Figure illustrates the appearance scale definition of), +, ++, and +++ as used in the Examples.

Provided herein are improved methods for preparing phospholipid-based ultrasound contrast agents (UCA). These improvements are based in part on the surprising discovery that certain phospholipid-based formulations, intended for use in preparing ultrasound contrast agents, are susceptible to the presence and amount of certain divalent metal cations. Specifically, it was unexpectedly found that divalent metal cations, such as calcium, at certain concentrations, when introduced into a phospholipid-based formulation used to generate the leading ultrasound contrast agent, DEFINITY®, caused phospholipid and potentially other components of the formulation to precipitate out of solution, thereby rendering the formulation unusable. Such formulations are typically made in large scale batches and thus the inadvertent addition of calcium, for example, would render an entire batch unusable. This can lead to reduced manufacturing capability.

It has also been found, surprisingly, that certain phospholipids are more susceptible to precipitation induced by the presence of divalent metal cations such as calcium. Specifically, DPPA in non-aqueous solvent such as propylene glycol is more likely to precipitate in the presence of certain concentrations of divalent metal cations such as calcium. This same sensitivity was not observed, or not observed to the same degree, with other phospholipids such as DPPC and DPPE. This differential precipitation profile can easily result in a phospholipid formulation, and ultimately a UCA, having a different phospholipid composition than planned or desired. Thus, not only can the presence of divalent metal cations reduce total yield of a UCA (e.g., due to the non-filterability of a precipitate-containing phospholipid formulation such as the phospholipid suspensions described herein), it can also interfere with the phospholipid distribution of the UCA. This is problematic because it may result in UCA formulations of wholly unknown phospholipid content. As is well known in the pharmaceutical arts, the composition of such UCA formulations must remain constant and robustly reproducible, and batch-to-batch variability must be avoided or minimized to the greatest extent possible.

This disclosure therefore provides improved methods for preparing phospholipid formulations such as phospholipid solutions and phospholipid suspensions, as described herein. These methods improve the yields of such formulations by reducing the likelihood of phospholipid precipitation. They also produce, in a more robust and reproducible manner, phospholipid formulations having their intended phospholipid profiles and distributions. These methods take advantage of the novel and surprising findings described herein and provide phospholipid formulations of the desired phospholipid content and proportion without resorting to detecting precipitate.

Phospholipid Formulations, Generally

Provided herein are methods for preparing improved phospholipid solutions, phospholipid suspensions and ultimately UCA formulations. As will be described in greater detail, in some instances, the UCA formulations may be formed from non-aqueous phospholipid solutions that are combined with a gas such as perflutren. In other instances, the UCA formulation may be formed from combining the non-aqueous phospholipid solution with an aqueous solvent to form a phospholipid suspension that is combined with a gas such as perflutren. These and other phospholipid-containing compositions are collectively referred to herein as phospholipid formulations. Each of the specific formulations will be described in greater detail below. The phospholipid formulations of this disclosure typically comprise the three phospholipids that are used in the manufacture of the FDA-approved DEFINITY® microspheres. These three phospholipids are (1) 1,2-dipalmitoyl-sn-glycero-3-phosphatidylcholine (referred to herein as DPPC), (2) 1,2-dipalmitoyl-sn-glycero-3-phosphatidic acid (referred to herein as DPPA), and (3) N-(methoxy polyethylene glycol 5000 carbamoyl)-1, 2-dipalmitoyl-sn-glycero-3-phosphatidylethanolamine (referred to herein as MPEG5000-DPPE).

In some instances, modified forms of one or more of these phospholipids may be used. For example, 1,2-dipalmitoyl-sn-glycero-3-phosphatidylethanolamine (DPPE) may be conjugated to polyethylene glycol (PEG). The PEG conjugated to DPPE, or to another phospholipid, may have a molecular weight (MW, or length) selected from 1000-10,000, in some non-limiting instances. More typically, the PEG may have a MW of about 5000, in which case it is referred to as PEG5000, and when conjugated to DPPE is referred to as PEG5000-DPPE. The PEG is typically conjugated to a phospholipid such as DPPE at the phospholipid head group rather than at the aliphatic chain end. The PEG may have a hydroxy or a methoxy terminus, and may be referred to as HO-PEG5000 or as MPEG5000, respectively.

When conjugated to a DPPE, as an example, the conjugate may be referred to as HO-PEG5000-DPPE or as MPEG5000-DPPE. The full chemical name of the latter conjugate is N-(methoxy polyethylene glycol 5000 carbamoyl)-1,2-dipalmitoyl-sn-glycero-3-phosphatidyletha-nolamine, mono sodium salt (referred to herein as MPEG5000-DPPE).

DPPA, DPPC and MPEG5000-DPPE may be used in molar percentages of about 77-90 mole % DPPC, about 5-15 mole % DPPA, and about 5-15 mole % DPPE, including MPEG5000-DPPE. Preferred ratios of each phospholipid include weight % ratios of 6.0 to 53.5 to 40.5 (DPPA:DPPC:MPEG5000-DPPE) or a mole % ratio of 10 to 82 to 8 (10:82:8) (DPPA:DPPC:MPEG5000-DPPE).

The remainder of this disclosure will refer specifically to DPPA, DPPC and MPEG5000-DPPE for convenience and brevity.

Various methods provided herein involve measuring the divalent metal concentration of the components used to make the phospholipid formulations described herein. Of particular importance are the components used to make the phospholipid solutions, particularly since precipitation appears to be a phenomenon first observed at the phospholipid solution step rather than at the phospholipid suspension step. Methods that may be used to measure divalent metal cation concentration, such as calcium and magnesium concentration, are described in greater detail herein including in the Examples. Some methods may involve measuring the divalent metal cation concentration of only one component, such as for example MPEG5000-DPPE. Other methods may involve measuring the divalent metal cation concentration of two or more of the components such as for example two or three of the phospholipids. In some embodiments, the components may be combined together before the measurement is made. Still other methods involve measuring the divalent metal cation concentration of all the components, including the non-aqueous solvent, used to make the phospholipid formulation such as the phospholipid solution. Such measurement may be made before or after the components are combined. For example, measurement may be made of individual components used to make a phospholipid solution or it may be made of the phospholipid solution itself.

Various other methods provided herein involve selecting components used to make the phospholipid formulations such as the phospholipid solutions, based on their divalent metal cation concentration. More specifically, the methods involve selecting one or more components that have been characterized or identified as having no or low divalent metal cation concentration, including no or low calcium concentration or no or low magnesium concentration. Some methods may involve selecting one component, such as MPEG5000-DPPE, characterized or identified as having no or low divalent metal cation concentration, including no or low calcium concentration or no or low magnesium concentration. Some methods may involve selecting two or more or all components based on their combined divalent metal cation concentration. Thus, it is contemplated that DPPA, DPPC and MPEG5000-DPPE, as well as other components such as but not limited to non-aqueous solvent and/or its individual components, may be individually characterized as having no or low divalent metal cation concentration but that when used together their combined divalent metal cation concentration will no longer satisfy the requirement of no or low divalent metal cation concentration and will cause precipitation. Thus, in these and other instances, two, three or all of the components such as two or three of the phospholipids may be selected such that their combined divalent metal cation concentration is characterized as no or low divalent metal cation concentration.

Phospholipid Solution

As used herein, a phospholipid solution refers to a composition comprising one or more phospholipids in a non-aqueous solvent. The phospholipid solution may minimally comprise DPPA, DPPC and MPEG5000-DPPE in a non-aqueous solvent.

A non-aqueous solvent, as used herein, is a solvent that causes phospholipids to dissolve thereby forming solution (i.e., a phospholipid solution). Preferably, the non-aqueous solvent present in the phospholipid solution is pharmaceutically acceptable, particularly since it is carried through to the final UCA formulation that is administered to a subject including a human subject. In certain embodiments, the non-aqueous solvent used to make the phospholipid solution is not or does not comprise methanol or toluene or methyl t-butyl ether (MTBE).

The non-aqueous solvent of the phospholipid solution may be a single solvent or it may be combination of solvents. Non-aqueous solvents include but are not limited to propylene glycol (which may be referred to herein as PG) and glycerol (which may be referred to herein as G). Both are provided as liquid stocks. In some instances, the non-aqueous solvent of the phospholipid solution may be PG alone or it may be a mixture of PG and G (which may be referred to as PG/G). A non-aqueous solvent that comprises at least PG may be referred to herein as a PG-comprising non-aqueous solvent. The PG/G mixtures include ratios ranging from 5:1 to 1:5 (weight by weight). In some embodiments, a PG:G w/w ratio of 1:1 is used (and is referred to herein as a 1:1 mixture).

The phospholipid solution may further comprise one or more buffers. Such buffers are those capable of buffering a non-aqueous solvent such as those recited above. Examples include, without limitation, an acetate buffer (e.g., a combination of sodium acetate and acetic acid), a benzoate buffer (e.g., a combination of sodium benzoate and benzoic acid), and a salicylate buffer (e.g., a combination of sodium salicylate and salicylic acid). Other buffers that may be used include a diethanolamine buffer, a triethanolamine buffer, a borate buffer, a carbonate buffer, a glutamate buffer, a succinate buffer, a malate buffer, a tartrate buffer, a glutarate buffer, an aconite buffer, a citrate buffer, a lactate buffer, a glycerate buffer, a gluconate buffer, and a tris buffer. In some embodiments, an acetate buffer is used. The buffer used in the non-aqueous solvent may be a non-phosphate buffer intending that it is not a phosphate buffer.

The buffer concentration will vary depending on the type of buffer used, as will be understood and within the skill of the ordinary artisan to determine. The buffer concentration in the non-aqueous solvent may range from about 1 mM to about 100 mM, including about 1 mM to about 50 mM, or about 1 mM to about 20 mM, or about 1 mM to about 10 mM, or about 1 mM to about 5 mM, including about 5 mM.

Accordingly, the phospholipid solution may comprise one or more phospholipids such as DPPA, DPPC and MPEG5000-DPPE, a non-aqueous solvent that is or that comprises PG, and optionally a buffer such as acetate buffer.

The phospholipid solution may be made in a number of ways, several of which are described in greater detail below. In general, the non-aqueous solvent may be warmed prior to contact with the phospholipids, and if used the buffer may first be present in the solvent prior to contact with the phospholipids. The solvent and then solution may be stirred to facilitate dissolution of the phospholipids.

Significantly, it has been found that phospholipid precipitation associated with divalent metal cations occurs in the non-aqueous solvent and thus in the process of making the phospholipid solution. Thus, as described herein various methods include steps of measuring divalent metal cation concentration of the various components used to make the phospholipid solution, including the phospholipids whether individually or collectively, the non-aqueous solvent such as the PG and G, the buffer such as the acetate buffer, if used, and the like.

In some embodiments, the divalent metal cation concentration of the phospholipid suspension may be measured, instead of or in addition to measuring the divalent metal cation concentration of the phospholipid solution.

A visual observation of the phospholipid solution may be made to detect precipitate, although this is not required. FIG. 1 is a photograph showing various phospholipid solutions having differing degrees of precipitate.

In some embodiments, the phospholipid solution is then used to prepare the phospholipid suspension described in greater detail below.

In some embodiments, the phospholipid solution is directly contacted with gas such as a perfluorocarbon gas to make phospholipid encapsulated gas microspheres, without first contacting the phospholipid solution with an aqueous solvent. That is, in some instances, the phospholipid-encapsulated gas microspheres are made through contact and vigorous shaking (referred to as activation) of the (non-aqueous) phospholipid solution and the gas. Such microspheres may then be contacted with an aqueous solvent to form a UCA.

Phospholipid Suspension

As used herein, a phospholipid suspension refers to an aqueous phospholipid formulation comprising phospholipid solution and an aqueous solvent. The phospholipid suspension may comprise one or more phospholipids such as DPPA, DPPC and MPEG5000-DPPE. A phospholipid suspension will minimally comprise one or more phospholipids such as one or more phospholipids, a non-aqueous solvent such as PG, and an aqueous solvent.

An aqueous solvent, as used herein, is or comprises water as its major component (by weight). An aqueous solvent may further comprise one or more salts, and thus may be referred to as an aqueous saline solvent. It may additionally or alternatively comprise a buffer, and thus may be referred to as an aqueous buffered saline solvent or an aqueous buffered solvent. Preferably, the aqueous solvent, regardless of whether it includes salt(s) or buffer(s) is pharmaceutically acceptable, since like the phospholipid solution it is carried through to the final UCA formulation that is administered to a subject including a human subject.

Salts that may be included in the aqueous solvent include but are not limited to sodium chloride.

Buffers that may be included in the aqueous solvent include but are not limited to phosphate buffer, acetate buffer, benzoate buffer, salicylate buffer, diethanolamine buffer, triethanolamine buffer, borate buffer, carbonate buffer, glutamate buffer, succinate buffer, malate buffer, tartrate buffer, glutarate buffer, aconite buffer, citrate buffer, lactate buffer, glycerate buffer, gluconate buffer, and a tris (tris (hydroxymethyl)methylamine) buffer. Typically, either the non-aqueous solvent or the aqueous solvent comprises a buffer, but not both. The buffer concentration will vary depending on the type of buffer used, as will be understood and within the skill of the ordinary artisan to determine. The buffer concentration in the aqueous solvent may range from about 1 mM to about 100 mM, including about 1 mM to about 50 mM, or about 10 mM to about 30 mM, or about 20 mM to about 30 mM, or about 20 mM to about 25 mM, including about 25 mM.

Accordingly, the phospholipid suspension may comprise one or more phospholipids such as DPPA, DPPC and MPEG5000-DPPE, a non-aqueous solvent that is or that comprises PG, an aqueous solvent that may comprise one or more salts such as sodium chloride, and optionally a buffer such as acetate buffer or a phosphate buffer. Phospholipid suspensions may be physically characterized as phospholipids suspended, rather than dissolved, in an aqueous solvent.

The phospholipid suspension is generally made by contacting the phospholipid solution, which is non-aqueous, with the aqueous solvent. The aqueous solvent may already comprise any salts and/or any buffers or alternatively those may be added after contact with the phospholipid solution. The aqueous solvent may be stirred in order to ensure mixing of the phospholipid solution with the aqueous solvent. The aqueous solvent may also be warmed prior to contacting with phospholipid solution which in some instances may also be warmed.

Surprisingly, the divalent metal cation concentration of the aqueous solvent is not as important as that of the non-aqueous phospholipid solution (and its combined components). For example, it has been found unexpectedly that once a precipitate-free phospholipid solution is prepared, it can be combined with an aqueous solvent that has a high divalent metal cation concentration without inducing any discernable phospholipid precipitate. Thus, it has been found surprisingly that the phospholipid sensitivity to high divalent metal cation content exists only in the phospholipid solution or in the presence of the non-aqueous solvent, but not beyond that point. Similarly, it has been found that once the precipitate is formed in the phospholipid solution, contact with the aqueous solvent, even if warmed, does not lead to its dissolution. This differential sensitivity of phospholipids, and in particular, DPPA to high divalent metal cation levels, such as calcium levels, was not heretofore appreciated and was considered a surprising finding.

While the divalent metal cation concentration of the aqueous solvent does not appear to induce precipitation of one or more phospholipids, it does surprisingly induce precipitation of other components, including most notably phosphate such as may be present if a phosphate buffer is used in the aqueous solvent. Thus, in some instances, the methods provided herein may further include measuring divalent metal cation concentration of components used to make the aqueous phospholipid suspensions that comprise phosphate. Alternatively, the methods may include selecting individual components or combined components that are characterized, individually or in combination, as having no or low divalent metal cation concentration.

The phospholipid suspension may then be used to prepare the phospholipid-encapsulated gas microspheres.

Phospholipid-Encapsulated Gas Microspheres, and UCA Formulations Comprising them As will be apparent, the phospholipid-based ultrasound contrast agents of this disclosure are phospholipid-encapsulated gas microspheres. These microspheres may be made in a number of ways. For example, a phospholipid solution may be contacted with an aqueous solvent to form a phospholipid suspension, and the phospholipid suspension may be contacted with a gas such as a perfluorocarbon gas to form the phospholipid-encapsulated gas microspheres. As another example, the non-aqueous phospholipid solution may be contacted with a gas such as a perfluorocarbon gas to form the phospholipid-encapsulated gas microspheres. In either instance, the phospholipid formulation, be it a non-aqueous phospholipid solution or an aqueous phospholipid suspension, is combined with the gas in a manner sufficient to create the phospholipid-encapsulated gas microspheres. This usually involves vigorous shaking or other agitation. Sufficient shaking or agitation is typically achieved using a device, such as a VIALMIX®, and is not typically achieved manually.

The phospholipid solution or the phospholipid suspension are provided in a container, such as a vial, having a gas headspace. A perfluorocarbon gas, such as perflutren, is introduced into the headspace of such containers, usually through a process of gas exchange. It is this vial that is then vigorously shaken in order to form the phospholipid-encapsulated gas microspheres. This process, known as activation, is carried out by the end user or medical personnel just prior to administration into a subject.

The microspheres comprise gas, such as a perfluorocarbon gas including but not limited to perflutren gas, in their internal cavity. The phospholipid shell that encapsulates the gas may be arranged as a unilayer or a bilayer, including unilamellar or multilamellar bilayers. The microspheres may have a mean diameter of less than 10 microns, or less than 6 microns, or less than 3 microns, or more preferably less than 2 microns. These mean diameters intend that, when a population of microspheres is analyzed, the mean diameter of the population is less than 10 microns, or less than 6 microns, or less than 3 microns, or more preferably less than 2 microns. The microspheres may have a mean diameter in the range of 0.5 to 3 microns, or 1 to 2 microns, or 1.4 to 1.8 microns, or 1.4 to 1.6 microns. The mean diameter may be about 1.4 microns.

The process of generating phospholipid-encapsulated gas microspheres is known as activation. Formulations that comprise a sufficient concentration of phospholipid-encapsulated gas microspheres may be referred to herein as activated formulations.

It will be appreciated that the concentration of the gas microspheres that is "sufficient" will depend on whether the gas microspheres are made using the phospholipid solution (without intervening use of an aqueous solvent) or are made using the phospholipid suspension. Typically, the UCA formulation being administered to a subject will comprise on the order of about at least $1 \times 10^7$ microspheres per ml of administered formulation, or at least $5 \times 10^7$ microspheres per ml, or at least $7.5 \times 10^7$ microspheres per ml, or at least $1 \times 10^8$ microspheres per ml, or at least $1 \times 10^9$ microspheres per ml, or about $5 \times 10^9$ microspheres per ml. The range of microsphere concentration may be, in some instances, $1 \times 10^7$ to $1 \times 10^{10}$ microspheres per ml of administered formulation, and more typically $5 \times 10^7$ to $5 \times 10^9$ microspheres per ml.

Depending on how they are made, the gas microspheres may be present in a non-aqueous solvent or in an aqueous solvent. Regardless, prior to administration to a subject, they are typically diluted in an aqueous solution that may be a saline solution, or a buffered aqueous solution, or a buffered saline solution.

The UCA formulation to be administered, typically intravenously, to a subject including a human subject may have a pH in the range of 4-8 or in a range of 4.5-7.5. In some instances, the pH may be in a range of about 6 to about 7.5, or in a range of 6.2 to about 6.8. In still other instances, the pH may be about 6.5 (e.g., 6.5+/−0.5 or +/−0.3). In some instances, the pH may be in a range of 5 to 6.5 or in a range of 5.2 to 6.3 or in a range of 5.5 to 6.1 or in a range of 5.6 to 6 or in a range of 5.65 to 5.95. In still another instance, the pH may be in a range of about 5.7 to about 5.9 (e.g., +/−0.1 or +/−0.2 or +/−0.3 either or both ends of the range). In another instance, the pH may be about 5.8 (e.g., 5.8+/−0.15 or 5.8+/−0.1).

The gas is preferably substantially insoluble in the phospholipid formulations provided herein, including the phospholipid solution and the phospholipid suspension. The gas may be a non-soluble fluorinated gas such as sulfur hexafluoride or a perfluorocarbon gas. Examples of perfluorocarbon gases include perfluoropropane, perfluoromethane, perfluoroethane, perfluorobutane, perfluoropentane, perfluorohexane. Examples of gases that may be used are described in U.S. Pat. No. 5,656,211 and are incorporated by reference herein. In an important embodiment, the gas is perfluoropropane.

Divalent Metal Cations, and Methods of Measuring Same

Divalent metal cations are divalent metal ions with a valence of 2. These include: barium(2+), beryllium(2+), cadmium(2+), calcium(2+), chromium(2+), cobalt(2+), copper(2+), europium(2+), gadolinium(2+), germanium(2+), iron(2+), lanthanum(2+), lead(2+), magnesium(2+), manganese(2+), mercury(2+), nickel(2+), osmium(2+), platinum(2+), ruthenium(2+), strontium(2+), tin(2+), uranium(2+), vanadium(2+), yttrium(2+), and zinc(2+).

In some embodiments, the divalent metal cations of interest are calcium, magnesium and manganese. In some embodiments, the divalent metal cations of interest are calcium and magnesium and therefore only calcium and magnesium are measured or components are selected based only on their calcium and magnesium content. In some embodiments, the divalent metal cation of interest is calcium, and therefore only calcium is measured or components are selected based on their calcium concentration.

Effect of Divalent Metal Cations

As described herein, divalent metal cations may be present in one or more of the components used to make the UCA formulations. Their presence may not be appreciated until such components are combined with the non-aqueous solvent to form the phospholipid solution, at which point phospholipid precipitation may be induced for example, or until such components are combined with the aqueous solvent to form the phospholipid suspension, at which point phosphate precipitation may be induced for example. Surprisingly, it was discovered in accordance with this disclosure that the MPEG5000-DPPE phospholipid stock contained calcium and magnesium at sufficiently high concentrations to cause precipitation of at least the DPPA phospholipid once combined. Thus, the divalent metal cations may have different effects on different phospholipids, and it may not be readily apparent to the user whether a phospholipid (or other component) contains such cations at concentrations sufficient to induce precipitation.

The inventors discovered in the process of preparing various UCA formulations that a non-aqueous solvent became cloudy when combined with a phospholipid blend comprising DPPA, DPPC and MPEG5000-DPPE phospholipids. It was further determined that the cloudy appearance was likely due to the precipitation of the DPPA phospholipid. Unbeknownst to the inventors, however, was the fact that the MPEG5000-DPPE contained high concentrations of calcium and magnesium ions and that those calcium and magnesium concentrations were likely the cause of the DPPA precipitation. Interestingly, such cations did not appear to affect the ability of MPEG5000-DPPE to remain in solution and thus a user would not appreciate that fact until such phospholipid was combined with the others in the non-aqueous mixture. Further studies, described in greater detail herein, found that precipitation occurred when a MPEG5000-DPPE stock later characterized as having a high calcium concentration was combined with DPPA, regardless of the order of addition or the presence of other components such as other phospholipids such as DPPC and DPPA. The sensitivity of DPPA to precipitate in a non-aqueous solvent comprising PG in the presence of sufficiently high divalent metal cation concentration such as calcium and magnesium concentration yet not in an aqueous solvent having similarly high concentrations of either or both calcium and magnesium was even more surprising. In other words, the concentrations of calcium that caused DPPA precipitation in non-aqueous solvent comprising PG did not cause DPPA precipitation in the aqueous solvent, and this too was surprising.

No or Low Divalent Metal Cation Concentration

As used herein, components are selected that are characterized or identified as having no or low divalent metal cation concentration, which includes no or low calcium concentration. Such divalent metal cation concentration is expressed as a weight by weight measure (i.e., weight of the divalent metal cation per unit weight of the underlying matrix or solvent in which the component of interest is present). A microgram per gram concentration may be alternatively referred to as parts per million or ppm.

A no or low calcium concentration of such component will further depend upon how much of that component is used or in other words how much such component is diluted to form the phospholipid solution or the phospholipid suspension.

In the simplest case, only one component is of interest, and only its calcium concentration is measured or only that component is selected based on its calcium concentration. Based on this disclosure, one of ordinary skill in the art will understand and be able to determine how much calcium will be tolerated in that component in order to avoid precipitation in the phospholipid solution or the phospholipid suspension.

As an example, calcium concentration in a phospholipid stock (which is typically provided as a solid such as a powder) is expressed in weight of calcium per gram of phospholipid. An example is a calcium weight per gram of MPEG5000-DPPE or calcium weight per gram DPPC. When two components such as two phospholipids are combined, the measure may be weight of calcium per gram of MPEG5000-DPPE and DPPC combined.

No divalent metal cation, such as no calcium, refers to a concentration of such cation that is undetectable using the methods known in the art and/or provided herein.

No or low divalent metal cation concentration in a phospholipid stock will depend on the particular component.

No or low divalent metal cation concentration in an MPEG5000-DPPE phospholipid stock is less than 510 micrograms/gram (i.e., micrograms of divalent metal cation per gram of MPEG5000-DPPE) (also referred to as less than 510 ppm), including less than 345 ppm, less than 230 ppm, less than 115 ppm, less than 57.5 ppm, and less than 11.5.

No or low divalent metal cation concentration in a DPPC phospholipid stock is less than 390 micrograms/gram (i.e., micrograms of divalent metal cation per gram of DPPC) (also referred to as less than 390 ppm), including less than 270 ppm, less than 180 ppm, less than 90 ppm, less than 45 ppm, and less than 9 ppm.

No or low divalent metal cation concentration in a DPPA phospholipid stock is less than 3440 micrograms/gram (i.e., micrograms of divalent metal cation per gram of DPPA) (also referred to as less than 3440 ppm), including less than 2340 ppm, less than 1560 ppm, less than 780 ppm, less than 390 ppm, and less than 78 ppm.

No or low divalent metal cation concentration in a phospholipid blend is less than 210 micrograms/gram (i.e., micrograms of divalent metal cation per gram of phospholipid blend or the combined weight of MPEG5000-DPPE and DPPC and DPPA) (also referred to as less than 210 ppm), including less than 150 ppm, less than 100 ppm, less than 50 ppm, less than 25 ppm, and less than 5 ppm.

No or low divalent metal cation concentration in propylene glycol is less than 3.1 micrograms/gram (i.e., micrograms of divalent metal cation per gram of propylene glycol) (also referred to as less than 3.1 ppm), including less than 2.1 ppm, less than 1.4 ppm, less than 0.7 ppm, less than 0.35 ppm, and less than 0.07 ppm.

No or low divalent metal cation concentration in a 1:1 (weight to weight) propylene glycol and glycerol mixture is less than 10.4 micrograms/gram (i.e., micrograms of divalent metal cation per gram of propylene glycol and glycerol combined) (also referred to as less than 10.4 ppm), including less than 7.8 ppm, less than 5.2 ppm, less than 2.6 ppm, less than 1.3 ppm, and less than 0.26 ppm.

No or low divalent metal cation concentration in glycerol is less than 20.4 micrograms/gram (i.e., micrograms of divalent metal cation per gram of glycerol) (also referred to as less than 20.4 ppm), including less than 15.3 ppm, less than 10.2 ppm, less than 5.10 ppm, less than 2.6 ppm, less than 0.51 ppm.

No or low divalent metal cation concentration in a phospholipid solution that comprises only propylene glycol as the non-aqueous solvent is less than 3.1 micrograms/gram (i.e., micrograms of divalent metal cation per gram of all components of the phospholipid solution) (also referred to as less than 3.1 ppm), including less than 2.1 ppm, less than 1.4 ppm. less than 0.7 ppm, less than 0.35 ppm, and less than 0.07 ppm. As will be appreciated based on the composition of the phospholipid solution, the major component by weight is the non-aqueous solvent, in this particular case, propylene glycol.

It is to be understood that the same concentration limits apply to calcium concentration and magnesium concentration, as well as combined calcium and magnesium concentrations.

This disclosure contemplates measurement of divalent metal cation concentration in one or more components of the phospholipid solution, including for example one, two or all three of the phospholipid stocks, optionally together with measurement of divalent metal cation concentration of the non-aqueous solvent such as propylene glycol and/or glycerol, depending on the nature of the phospholipid solution. If any of these components contain a divalent metal cation concentration in excess of those levels recited above, then it is expected that once a phospholipid solution is made with such component, such phospholipid solution will be prone to precipitation.

Some embodiments contemplate that a single component will be analyzed for its divalent metal cation concentration and that if such concentration is a "no or low divalent metal cation concentration" then the component may be combined with the remaining components even if such components were not analyzed for their divalent metal cation concentration. Components of a phospholipid solution include the phospholipid stocks, whether provided individually or as a blend, non-aqueous solvents such as propylene glycol and glycerol, and optionally buffers.

Some embodiments contemplate that more than one but less than all components of the phospholipid solution will be measured for their divalent metal cation concentration. In some instances, if one of the components have a divalent metal cation concentration that is in excess of the "no or less divalent metal cation concentration" limit listed above, then it may not be used to prepare the phospholipid solution (or phospholipid blend). In some instances, no one component may be characterized or identified as having a divalent metal cation concentration that is more than the "no or low divalent metal cation concentration". However, when such components are used in combination, the combined divalent metal cation concentration may be determined based on the amount each contributes to the phospholipid solution. It is contemplated that the combined divalent metal cation concentration may or may not exceed the "no or low divalent metal cation concentration" as defined above for the phospholipid solution.

As discussed throughout, the various levels set forth herein while referring to divalent metal cations, apply equally to calcium. The Examples demonstrate that the lowest calcium concentration at which precipitation of phospholipid is apparent is about 0.7 microgram calcium per gram of non-aqueous solvent (see Examples 1 and 2), otherwise referred to as about 0.7 ppm. Thus, a no or low divalent metal cation concentration such as a no or low calcium concentration in a non-aqueous phospholipid solution is less than 0.7 ppm, less than 0.35 ppm, or less than 0.07 ppm. It is to be understood that a divalent metal cation concentration in the phospholipid solution of less than 0.7 ppm will also be regarded as a no or low divalent metal ion concentration.

Divalent metal cation concentration in an aqueous phospholipid suspension may be provided as a weight of divalent metal cation per gram of aqueous solvent. Typically, the phospholipid suspension is formed by diluting the non-aqueous phospholipid solution about 20-fold into the aqueous solvent. Thus, a no or low divalent metal ion concentration in a phospholipid suspension is less than 0.035 micrograms per gram of phospholipid suspension. Similarly, the calcium concentration in a phospholipid suspension originating from the phospholipid solution is less than 0.035 micrograms per gram of phospholipid suspension.

The concentration at which the divalent metal cations cause phospholipids to precipitate may be temperature dependent. At higher temperatures, higher concentrations of cations may be tolerated before precipitation is observed. At lower temperatures, lower concentrations of cations may cause the precipitation to occur.

As an example, at temperatures of about 55° C. (e.g., 50-60° C.), no or low divalent metal cation concentration is a divalent metal cation concentration of less than 0.7 micrograms calcium per gram of phospholipid solution or of non-aqueous solvent. This level may be slightly lower if the phospholipid solution is prepared at a lower temperature. Alternatively, this level may be slightly higher if the phospholipid solution is prepared at a higher temperature.

Calcium Sources

As demonstrated in the Examples, the phospholipid solution is unexpectedly and uniquely sensitive to particular levels of calcium. This unique sensitivity was not heretofore recognized. Given the effect of calcium on the preparation of the phospholipid solution, and thus ultimately on the UCA, it is important to measure and thus control the calcium concentration of the phospholipid solution. Calcium may be present in each of the components of the phospholipid solution, including the phospholipid stocks and the non-aqueous solvents, as described below.

Calcium and magnesium are divalent alkaline earth metals in group 2 of the periodic table. Calcium is the fifth-most-abundant element by mass in the Earth's crust and the cation Ca2+ is also the fifth-most-abundant dissolved ion in seawater. It is found at various levels in tap water depending on the on the "hardness". The total water hardness is the sum of the molar concentrations of Ca2+ and Mg2+, ranging from soft at 0-60 ppm to very hard ≥181.

Calcium and magnesium are also found in varying concentration in the crude glycerol extract from biodiesels. Level of calcium and magnesium were reported to range from 12 to 163 ppm and 4 to 127 ppm respectively depending on the seed oil for biodiesel production (J. C. Thompson 2006 Applied Engineering in Agriculture Vol. 22(2): 261-265). A major supply of glycerol comes from this biodiesel byproduct. The crude glycerol extract can be purified by treatment with activated carbon to remove organic impurities, alkali to remove unreacted glycerol esters, and ion exchange to remove salts. High purity glycerol (>99.5%) is obtained by multi-step distillation; vacuum is helpful due to the high boiling point of glycerol (290° C.).

Industrially, propylene glycol is produced from propylene oxide. Different manufacturers use either non-catalytic high-temperature process at 200° C. (392° F.) to 220° C. (428° F.), or a catalytic method, which proceeds at 150° C. (302° F.) to 180° C. (356° F.) in the presence of ion exchange resin or a small amount of sulfuric acid or alkali. Final products contain 20% propylene glycol, 1.5% of dipropylene glycol and small amounts of other polypropylene glycols. Further purification produces finished industrial grade or USP/JP/EP/BP grade propylene glycol that is typically 99.5% or greater. Propylene glycol can also be converted from glycerol, a biodiesel byproduct.

The calcium and magnesium contents of Pharmacopeia grade propylene glycol and glycerol are not quantified as a certificate of analysis requirement of US Pharmacopeia, European Pharmacopeia, British Pharmacopeia or Japanese Pharmacopeia.

Phospholipid DPPA contains a phosphate which can be ionized at appropriate pH. The pKa for the two hydroxyl groups of the phosphate are 6.2 and 1.8 (Tatulian Ionization and Binding, 511-552 Phospholipid Handbook, Ed. G Ceve 1993). DPPA is commercially available as different salt forms. Usually, the Na salt is used but the Ca salt is also available.

DPPC is a zwitterion and therefore does not require a counter ion.

MPEG5000-DPPE is a modified DPPE which has a pKa of 1.9 and 9.3 for the hydroxyl of the phosphate and the amine of the ethanolamine (Tatulian Ionization and Binding, 511-552 Phospholipid Handbook, Ed. G Ceve 1993). MPEG500-DPPE is available as the Na salt form.

Methods of Measuring Divalent Metal Cation Concentration

Quantitation of divalent metal cations concentration can be performed using one of several known techniques. These include atomic spectroscopy methods such as atomic absorption spectroscopy (AAS), flame photometry or flame atomic emission spectrometry (FAES), inductively coupled plasma-atomic emission spectrometry (ICP-AES), and other methods such as inductively coupled plasma-mass spectroscopy or complexometric titration. The spectroscopic approaches utilize absorption or emission characteristics of the metal ions of alkali metals (Group 1) and alkaline earth metals (Group II) metals when dissociated due to thermal energy provided by a flame source. ICP-MS is a type of mass spectrometry which is capable of detecting metals at very low concentrations. This is achieved by ionizing the sample with inductively coupled plasma and then using a mass spectrometer to separate and quantify those ions. Some of these methods are used in the Examples.

Complexometric titration is another method for detecting divalent metal cation concentration. This method uses EDTA (ethylenediaminetetraacetic acid) complexation with calcium and magnesium ions to compete with a color indicator. This allows rapid colorimetric quantitation. EDTA forms a complex with calcium and magnesium ions. A blue dye called Eriochrome Black T (ErioT) is used as the indicator. This blue dye also forms a complex with the calcium and magnesium ions, changing color from blue to pink in the process. The dye-metal ion complex is less stable than the EDTA-metal ion complex. For the titration, the sample solution containing the calcium and magnesium ions is reacted with an excess of EDTA. The indicator is added and remains blue as all the Ca2+ and Mg2+ ions present are complexed with the EDTA.

A back titration is carried out using a solution of magnesium chloride. This forms a complex with the excess EDTA molecules until the end-point, when all the excess EDTA has been complexed. The remaining magnesium ions of the magnesium chloride solution then start to complex with ErioT indicator, immediately changing its color from blue to pink Methods of Synthesis The disclosure provides methods for preparing phospholipid solutions and phospholipid suspensions intended for use with a perfluorocarbon gas to form a UCA formulation comprising phospholipid-encapsulated gas microspheres. In preferred embodiments, the phospholipids are DPPA, DPPC and DPPE such as MPEG5000-DPPE.

The phospholipid solution may be made in a number of ways, as described below. These methods are characterized broadly as blend and non-blend methods. The starting phospholipid stocks may be in solid (e.g., powder) form or in liquid form.

Blend Methods

Blend methods refer to methods in which the phospholipids are intimately blended with each other in order to render a solid phospholipid mixture that is more uniform (and thus more homogenous) with respect to its phospholipid content and phospholipid distribution and in some instances has higher purity, as compared to simple mixtures of phospholipids.

This method creates a homogenous dispersion of the three phospholipids by dissolving or suspending them in an appropriate blend solvent system, and then separates the evenly distributed phospholipids from the solvent. The separation of the blend solvent from the phospholipids can involve drying, lyophilization, distillation, and the like, or it can include precipitation using an additional blend solvent. Blend solvents for neutral lipids are relatively non-polar solvents such as diethyl ether or chloroform. More polar blend solvents such as alcohol (e.g., methanol and ethanol) are required for membrane-associated lipids which are themselves more polar. Chloroform may also be used, particularly for lipids of intermediate polarity. When mixed with methanol, chloroform becomes a general solvent. Dichloromethane (or methylene dichloride) is a similar extractant but less oxidizable. Hexane may be used for lipids of low polarity. It can be used to extract neutral lipids from water/alcohol mixtures. Petroleum ether is a mixture of various hydrocarbons with 5-8 carbon atoms and may be used in place of hexanes in some instances. Other blend solvents include without limitation cyclohexane and toluene.

As will be described in greater detail herein, certain blends are formed by contacting one or more desired phospholipids (e.g. DPPA, DPPC and MPEG5000-DPPE) in a blend solvent system to first dissolve such phospholipids, optionally then concentrating such solution, then either removing the blend solvent or precipitating the phospholipid blend from such solvent. The blend solvent is not to be confused with the non-aqueous solvent that is later used to dissolve the phospholipids, thereby forming a phospholipid solution. It should also be clear that this precipitation is a desired event and is not to be confused with the undesirable phospholipid precipitation that can occur during the later step of forming the phospholipid solution by the presence of calcium, another divalent cation, or a combination of divalent cations.

Some methods of preparing phospholipid solutions involve contacting a phospholipid blend with the non-aqueous solvent. There are various ways of making phospholipid blends, including but not limited to organic solvent (or blend solvent, as used herein) dissolution-precipitation methods and aqueous suspension-lyophilization methods.

The organic solvent dissolution-precipitation method is described in detail in U.S. Pat. No. 8,084,056 and in published International Application No. WO99/36104, the entire contents of both of which are incorporated herein by reference. One embodiment of this method involves the following steps:

(a) Contacting the desired phospholipids (e.g., DPPA, DPPC, and MPEG5000-DPPE) with a first blend solvent system. This system is typically a combination of solvents, for example $CHCl_3$/MeOH, $CH_2Cl_2$/MeOH, and toluene/MeOH. It may be desirable to warm the resultant solution to a temperature sufficient to achieve complete dissolution. Such a temperature is preferably about 25 to 75° C., more preferably about 35 to 65° C. After dissolution, undissolved foreign matter may be removed by hot-filtration or cooling to room temperature and then filtering. Known methods of filtration may be used (e.g., gravity filtration, vacuum filtration, or pressure filtration).

(b) The solution is then concentrated to a thick gel/semisolid. Concentration is preferably done by vacuum distillation. Other methods of concentrating the solution, such as rotary evaporation, may also be used. The temperature of this step is preferably about 20 to 60° C., more preferably 30 to 50° C.

(c) The thick gel/semisolid is then dispersed in a second blend solvent. The mixture is slurried, preferably near ambient temperature (e.g., 15-30° C.). Useful second blend solvents are those that cause the phospholipids to precipitate. The second blend solvent is preferably methyl t-butyl ether (MTBE). Other ethers and alcohols may be used.

(d) The solids produced upon addition of the second blend solvent are then collected. Preferably the collected solids are washed with another portion of the second blend solvent (e.g., MTBE). Collection may be performed via vacuum filtration or centrifugation, preferably at ambient temperature. After collection, it is preferred that the solids are dried in vacuo at a temperature of about 20-60° C.

The resultant solid is referred to herein as a phospholipid blend.

Certain of the methods described herein use phospholipids in the form of a phospholipid blend, including a phospholipid blend made according to any of the blend methods set forth above. Some methods use phospholipid blends, excluding the phospholipid blend made according to the methanol/toluene/MTBE method set forth above wherein a methanol and toluene mixture is used as the first blend solvent and MTBE is used as the second blend solvent. For clarity, the method set forth above is referred to herein as the methanol/toluene/MTBE phospholipid blend method.

As used herein, a phospholipid blend is distinguished from other phospholipid mixtures, including those mixtures that are made from simply combining phospholipids in their solid (including powder) forms, as described herein.

In the aqueous suspension-lyophilization methods, phospholipids are suspended in water at an elevated temperature and then concentrated by lyophilization.

The organic solvent dissolution-precipitation process is preferred over the aqueous suspension/lyophilization process for a number of reasons as outlined in U.S. Pat. No. 8,084,056 and published PCT application WO 99/36104, including the uniformly distributed phospholipid solid that results using the organic dissolution method.

Some blend methods that are not the methanol/toluene/MTBE phospholipid blend method recited above use a blend solvent system other than methanol and toluene. In these methods, the phospholipids are combined in a methanol-free and toluene-free condition (also referred to as a methanol and toluene-free condition) to form a phospholipid blend. Thus, a methanol and toluene-free condition refers to a condition that does not include both of these solvents.

Some blend methods combine the phospholipids in an blend solvent to form the phospholipid blend and then evaporate the blend solvent completely, for example either by drying or distillation, to form the dried phospholipid blend. It is this dried phospholipid blend that is then contacted with the non-aqueous solvent such as PG in the methods provided herein.

Some blend methods combine the phospholipids in an aqueous solvent and then lyophilize the mixture to form a lyophilized phospholipid composition. Other blend methods combine the phospholipids with other solvent systems such as but not limited to (1) an ethanol and cyclohexane (e.g., 1:1, v:v) mixture, and (2) tertiary butanol (t-butanol or 1,1 dimethyl ethanol), in place of water. Following dissolution in these various solvents, the compositions are lyophilize. Lyophilization can be performed by freezing over an isopropanol/CO2 bath or an acetone/CO2 bath and drying on a Virtis Lyophilizer until the product appears dry and flocculent in appearance.

Various blend methods that are not the methanol/toluene/MTBE phospholipid blend method recited above are described in published EP 0923383 (WO1997040858), the entire contents of which are incorporated by reference herein.

Some blend methods that are not the methanol/toluene/MTBE phospholipid blend method recited above combine the phospholipids in a blend solvent, which may be a mixture of toluene and methanol, to form a phospholipid blend, and then precipitate such phospholipid blend in the absence of MTBE. In these methods, the precipitation occurs in an MTBE-free condition.

In other blend methods, DPPA, DPPC and MPEG5000-DPPE may be combined in their dry, solid forms and such combination then may be actively and intimately mixed in dry form (e.g., manually stirring the powders or using a mixing device such as a tumbler silo mixer, an orbiting screw mixer, a ribbon mixer, an extruder, a cyclomix, a henschel mixer, a lodige type mixer, an Eirich type mixer, or other type of device designed for pharmaceutical powder mixing, with the aim of preparing a uniform blend of phospholipids (e.g., uniform phospholipid dispersion throughout the mixture). Reference can be made to Deveswaran et al. Research J. Pharm. and Tech.2 (2): April.-June. 2009) for additional methodologies for generating a uniform dry product.

Non-Blend Methods

In contrast to blend methods, certain non-blend methods involve simple mixing of solid phospholipids and this tends to result in a less uniform (and thus less homogenously dispersed or more heterogeneously dispersed) mixture. These latter mixtures are referred to herein as phospholipid mixtures (or non-blend phospholipid mixtures) in order to distinguish them from phospholipid blends.

Some ways of preparing phospholipid solutions involve simply contacting phospholipids in their solid forms with the non-aqueous solvent. The phospholipids may be contacted with the non-aqueous solvent simultaneously or sequentially. If sequentially, any order of addition may be used. The phospholipids may be added individually to the non-aqueous solvent or they may be first combined together, in any combination, and then added to the non-aqueous solvent. Thus, it is contemplated that the phospholipids may be added to the non-aqueous solvent individually and simultaneously, individually and sequentially, combined and simultaneously, and partially combined and sequentially. An example of the latter is an instance where two of the phospholipids are combined together in solid form and then contacted with the non-aqueous solvent before or after the remaining phospholipid is contacted with the non-aqueous solvent.

Thus, as an example, DPPA, DPPC and MPEG5000-DPPE phospholipids may be added individually to a non-aqueous solvent. Such individual addition may be sequential or simultaneous addition. If sequential, the order of addition can be any order although in some instances DPPA may be added second or last since it is the least abundant and least soluble and its dissolution can be facilitated by the presence of one of the other phospholipids. In some instances, regardless of whether the phospholipids are provided as individually, or as a simple mixture, or as a phospholipid blend, they are then dissolved in a non-aqueous solvent comprising PG or a PG/G mixture, as described above to form the phospholipid solution. The phospholipid solution may be combined with gas or it may combined with an aqueous solvent to form a phospholipid suspension which in turn is contacted with gas.

In other instances, a phospholipid blend may be prepared by combining the phospholipids in, for example, water, or in an ethanol and cyclohexane (e.g., 1:1, v:v) mixture, or in tertiary butanol (t-butanol or 1,1 dimethyl ethanol), and such mixture is then lyophilized, and the dried product is resuspended in an aqueous solvent. In these instances, the final resuspended product may be combined with a gas such as perflutren. This disclosure contemplates that any or all components used in this preparation may be analyzed for their divalent metal cation concentration, and such individual or combined divalent metal cation concentration may be quantified and used to select and/or prepare a UCA.

Methods of Preparing Ultrasound Contrast Agent, Including Activation

Phospholipid encapsulated gas microspheres are formed by combining and vigorously shaking a phospholipid solution or a phospholipid suspensions with a gas such as a perfluorocarbon gas. This process is referred to herein as activation. The UCA formulation so formed minimally comprises phospholipids, non-aqueous solvent such as PG, and gas, and thus activation minimally results in gas-filled phospholipid microspheres. The phospholipids may be present in an aqueous solution such as is the case with DEFINITY®, or they may be present in a non-aqueous solution such as is the case with novel UCA formulations including for example DEFINITY-II, described in greater detail herein. Thus, in some instances, activation comprises shaking an aqueous phospholipid suspension in the presence of a gas, such as a perfluorocarbon gas (e.g., perflutren). In other instances, activation comprises shaking a phospholipid solution in the presence of a gas, a perfluorocarbon gas (e.g., perflutren). It is to be understood that perflutren, perflutren gas and octafluoropropane gas are used interchangeably herein.

Shaking, as used herein, refers to a motion that agitates a solution, whether aqueous or non-aqueous, such that gas is introduced from the local ambient environment within the container (e.g., vial) into the solution. Any type of motion that agitates the solution and results in the introduction of gas may be used for the shaking. The shaking must be of sufficient force or rate to allow the formation of foam after a period of time. Preferably, the shaking is of sufficient force or rate such that foam is formed within a short period of time, as prescribed by the particular UCA formulation. Thus in some instances such shaking occurs for about 30 seconds, or for about 45 seconds, or for about 60 seconds, or for about 75 seconds, or for about 90 seconds, or for about 120 seconds, including for example for 30 seconds, or for 45 seconds, or for 60 seconds, or for 75 seconds, or for 90 seconds, or for 120 seconds. In some instances, the activation may occur for a period of time in the range of 60-120 seconds, or in the range of 90-120 seconds.

The disclosure contemplates that, in some instances, the shaking time (or duration) will vary depending on the type of UCA formulation being activated. For example, in some instances, an aqueous UCA formulation may be shaken for shorter periods of time than a non-aqueous UCA formulation. The disclosure contemplates that, in such instances, the shaking rate (or shaking speed, as those terms are used interchangeably herein) may be constant. Thus an activation or shaking means such as an activation or shaking device may be set to shake at one rate (defined in terms of number of shaking motions per minute, for example) for two or more different pre-determined periods of time.

The disclosure further contemplates that, in some instances, the shaking rate will vary depending on the type of UCA formulation being activated. For example, in some instances, an (aqueous) phospholipid suspension may be shaken at a slower shaking rate than a (non-aqueous) phospholipid solution. The disclosure contemplates that, in such instances, the shaking time (or duration, as those terms are used interchangeably herein) may be constant.

DEFINITY® may be activated with a VIALMIX®, as described below. DEFINITY® activation, which involves vigorous shaking of an (aqueous) phospholipid suspension in the presence of perflutren, lasts for about 45 seconds with a VIALMIX®. Unless indicated otherwise, the term "about" with respect to activation time intends a time that is +/−20% of the noted time (i.e., 45+/−9 seconds).

DEFINITY-II may be activated with a VIALMIX® as well. DEFINITY-II activation, which involves vigorous shaking of a (non-aqueous) phospholipid solution in the presence of perflutren, lasts for about 60 to 120 seconds. In some instances, DEFINITY-II is activated for about 75 seconds (i.e., 75+/−15 seconds). DEFINITY-II may be activated for longer periods of time including 90-120 seconds The shaking may be by swirling (such as by vortexing), side-to-side, or up and down motion. Further, different types of motion may be combined. The shaking may occur by shaking the container (e.g., the vial) holding the aqueous or non-aqueous phospholipid solution, or by shaking the aqueous or non-aqueous solution within the container (e.g., the vial) without shaking the container (e.g., the vial) itself. Shaking is carried out by machine in order to standardize the process. Mechanical shakers are known in the art and their shaking mechanisms or means may be used in the devices of the present disclosure. Examples include amalgamators such as those used for dental applications. Vigorous shaking encompasses at least 1000, at least 2000, at least 3000, at least 4000, at least 4500, at least 5000 or more shaking motions per minute. In some instances, vigorous shaking includes shaking in the range of 4000-4800 shaking motions per minute. VIALMIX® for example targets shaking for 4530 "figure of eight" revolutions per minute, and tolerates shaking rates in the range of 4077-4756 revolutions per minute. Vortexing encompasses at least 250, at least 500, at least 750, at least 1000 or more revolutions per minute. Vortexing at a rate of at least 1000 revolutions per minute is an example of vigorous shaking, and is more preferred in some instances. Vortexing at 1800 revolutions per minute is most preferred.

The shaking rate can influence the shaking duration needed. A faster shaking rate will tend to shorten the duration of shaking time needed to achieve optimal microbubble formation. For example, shaking at 4530 rpm for a 45 second duration will achieve 3398 total revolutions on a VIALMIX®. Shaking at 3000 rpm would require 68 seconds to achieve the same number of revolutions. The duration and shake speed required will also be influenced by the shape of the travel path and amplitude of shaking. The velocity the liquid in the container reaches and the forces exerted upon change of direction will influence gas incorporation. These aspects will be impacted upon based on the shaker arm length and path, the container shape and size, the fill volume and the formulation viscosity. Water has a viscosity of approximately 1.14 cps at 15° C. (Khattab, I. S. et al., Density, viscosity, surface tension, and molar volume of propylene glycol+water mixtures from 293 to 323 K and correlations by the Jouyban-Acree model Arabian Journal of Chemistry (2012). In contrast, propylene glycol has a viscosity of 42 cps at 25° C. (Khattab, I. S. et al., Density, viscosity, surface tension, and molar volume of propylene glycol+water mixtures from 293 to 323 K and correlations by the Jouyban-Acree model Arabian Journal of Chemistry (2012) and glycerol has a viscosity of 2200 cps at 15° C. (Secut J B, Oberstak HE Viscosity of Glycerol and Its Aqueous Solutions. Industrial and Engineering Chemistry 43. 9 2117-2120 1951). DEFINITY-II has a high viscosity of 1150 cps at 15° C. Since DEFINITY® is predominantly water it has a much lower viscosity than DEFINITY-II.

The formation of gas-filled microspheres upon activation can be detected by the presence of a foam on the top of the aqueous or non-aqueous solution and the solution becoming white.

Activation is carried out at a temperature below the gel state to liquid crystalline state phase transition temperature of the phospholipid employed. By "gel state to liquid crystalline state phase transition temperature", it is meant the temperature at which a phospholipid layer (such as a lipid monolayer or bilayer) will convert from a gel state to a liquid crystalline state. This transition is described for example in Chapman et al., J. Biol. Chem. 1974 249, 2512-2521. The gel state to liquid crystalline state phase transition temperatures of various phospholipids will be readily apparent to those skilled in the art and are described, for example, in Gregoriadis, ed., Liposome Technology, Vol. I, 1-18 (CRC Press, 1984) and Derek Marsh, CRC Handbook of Lipid Bilayers (CRC Press, Boca Raton, Fla. 1990), at p. 139. Vigorous shaking can cause heating of the formulation based on the shake speed, duration, shaker arm length and path, the container shape and size, the fill volume and the formulation viscosity.

It will be understood by one skilled in the art, in view of the present disclosure, that the phospholipids or phospholipid microspheres may be manipulated prior to or subsequent to being subjected to the methods provided herein. For example, after the shaking is completed, the gas-filled microspheres may be extracted from their container (e.g., vial). Extraction may be accomplished by inserting a needle of a syringe or a needle-free spike (e.g., PINSYNC®) into the container, including into the foam if appropriate, and drawing a pre-determined amount of liquid into the barrel of the syringe by withdrawing the plunger or by adding an aqueous liquid, mixing and drawing a pre-determined amount of liquid into the barrel of the syringe by withdrawing the plunger. As another example, the gas-filled microspheres may be filtered to obtain microspheres of a substantially uniform size. The filtration assembly may contain more than one filter which may or may not be immediately adjacent to each other.

Methods of Using Ultrasound Contrast Agent to Image a Subject

Also provided herein are methods of use of phospholipid-encapsulated gas microspheres and formulations thereof. The gas microspheres and formulations thereof may be used in vivo in human or non-human subjects, or they may be used in vitro. They may be used for diagnostic or therapeutic purposes or for combined diagnostic and therapeutic purposes.

When used in human subjects, phospholipid-encapsulated gas microspheres and formulations thereof may be used directly (neat) or may be diluted further in a solution, including a pharmaceutically acceptable solution, and administered in one or more bolus injections or by a continuous infusion. Administration is typically intravenous injection. Imaging is then performed shortly thereafter. The imaging application can be directed to the heart or it may involve another region of the body that is susceptible to ultrasound imaging. Imaging may be imaging of one or more organs or regions of the body including without limitation the heart, blood vessels, the cardiovasculature, the liver, the kidneys and the head.

Subjects of the invention include but are not limited to humans and animals. Humans are preferred in some instances. Animals include companion animals such as dogs and cats, and agricultural or prize animals such as but not limited to bulls and horses.

UCAs are administered in effective amounts. An effective amount will be that amount that facilitates or brings about the intended in vivo response and/or application. In the context of an imaging application, such as an ultrasound application, the effective amount may be an amount of phospholipid-encapsulated gas microspheres that allow imaging of a subject or a region of a subject.

EXAMPLES

1 Examples Methods
1.1 Phospholipids and Phospholipid Blends and Reagents

Phospholipids were used as either individual powders, combined together as powders and used as a mixture or blended together by dissolving and drying (details described below). The measured content of the individual phospholipids was used to estimate the final calcium or magnesium concentrations in the non-aqueous concentrate or the aqueous preparation unless direct measurements in the blend was made. Solvents with low calcium were used for all studies.

1.1.1 Phospholipid Blend

One phospholipid blend (LB) was prepared by dissolving DPPC, DPPA, MPEG5000-DPPE (0.401:0.045:0.304 [wt:wt:wt]) in toluene/methanol, concentrated with vacuum and warming and then slurried by the addition of Methyl t-butyl ether (MTBE). The solid material was collected, washed with MTBE and dried (consistent with U.S. Pat. No. 8,084, 056). Alternatively, DPPC, DPPA, and MPEG5000-DPPE (0.401:0.045:0.304 [wt:wt:wt]) were solubilized at 55° C. in methanol. The methanol was then evaporated and the solids recovered as phospholipid blend. Similarly, DPPC, DPPA, and MPEG5000-DPPE (0.401:0.045:0.304 [wt:wt:wt]) were combined together as solid powders and the powders were mixed together with a spatula.

1.1.1.1 Residual Solvent Method for Phospholipid Blend

Residual solvent in phospholipid blend was determined by FID using GC headspace. Sample was weighed, transferred into a separate 20 cc headspace vials and dissolved in N-methylpyrrolidone. A set of residual solvent standards was prepared in N-methylpyrrolidone. Standards and samples were analyzed by FID using GC headspace. The concentration of each residual solvent was calculated from the calibration curve for that solvent.

1.1.2 Calcium measurements

Calcium levels were quantified in individual lipid, lipid blend, glycerol and propylene glycol using either ICP-MS or AA. Magnesium and other metal ions were also measured with these methods in some samples 1.1.1.2 ICP-MS (Inductively coupled plasma-mass spectrometry) method Samples were prepared by weighing into a pre-cleaned quartz digestion vessel. Matrix spikes were added and then mixed with nitric acid and hydrochloric acid. The samples were digested in a closed-vessel microwave digestion system. After cooling internal standard solution were added and diluted and analyzed by ICP-MS using He collision mode.

1.1.1.3 AA (Atomic Absorption Spectroscopy) Method

Samples were prepared by weighing into a dry "trace metals cleaned" digestion vessel and dissolved with nitric acid and hydrochloric acid and reflux with $H_2O_2$. The sample solution was washed with water and filtered. A set of standards were used to calibrate the AA and then the absorbance of the samples read from the calibration curve. Results for individual lipid, phospholipid blend, and formulations solvents are provided in Table 1.

TABLE 1

$Ca^{+2}$ and $Mg^{+2}$ Level in Individual Lipid, Lipid Blend and Solvent[a]

| Materials | $Ca^{+2}$ (ppm)[b] | $Mg^{+2}$ (ppm)[b] |
|---|---|---|
| Phospholipid Blend, Lot 1[c] | Not detected | Not detected |
| Phospholipid Blend Lot 2[c,d] | 370 | 54 |
| MPEG5000-DPPE (high $Ca^{+2}$) Lot 1 | 980 | 150 |
| MPEG5000-DPPE (high $Ca^{+2}$) Lot 2 | 520 | 110 |
| MPEG5000-DPPE (low $Ca^{+2}$) | 4 | Not determined |
| DPPC Lot 1 | Not detected | Not detected |
| DPPC Lot 2 | 7 | Not determined |
| DPPA | 19 | Not determined |
| Propylene glycol | Not detected | Not determined |
| Glycerol | 0.7 | Not determined |

[a]Determined by ICP-MS
[b]ppm = parts per million and is equivalent to μg/g
[c]Phospholipid blend consists of DPPC, DPPA and MPEG5000-DPPE (0.401:0.045:0.304 [wt:wt:wt])
[d]Lipid blend, Lot 2 prepared using MPEG5000-DPPE (high $Ca^{+2}$) Lot 1

1.2 Aqueous Formulation Preparation 1.2.1 Non-Aqueous Phospholipid Concentrate:

Phospholipid concentrates were prepared by adding the individual lipids (DPPC, DPPA, and MPEG5000-DPPE low $Ca^{+2}$, or MPEG5000-DPPE high $Ca^{+2}$, or a combination) in any order, adding phospholipid blend (LB), or adding LB containing high levels of $Ca^{+2}$ to 25-115 mL of propylene glycol (PG), or 1:1 v/v propylene glycol/glycerol (PG/G), or glycerol vehicle with constant stirring at 55° C. to 70° C. In some cases, lipid concentrate was prepared without DPPA or with calcium acetate added prior to lipid addition.

1.2.2 Aqueous Formulation:

Aqueous formulations were prepared by adding: dibasic sodium phosphate, heptahydrate; monobasic sodium phosphate, monohydrate; sodium chloride; propylene glycol; glycerol and finally non-aqueous phospholipid concentrate to 400 to 500 mL of water with constant stirring at 55° C. to 70° C. In some cases, calcium acetate was added prior to, or after addition of the non-aqueous phospholipid concentrate to the bulk compounding solution. In other cases the phosphate buffer was not included.

1.3 Non-Aqueous Formulation Preparation 1.3.1 Non-Aqueous Formulation

Individual lipids (DPPC, DPPA, and MPEG5000-DPPE low $Ca^{+2}$ or MPEG5000-DPPE high $Ca^{+2}$, or a combination of both) in any order, LB, or LB containing high levels of $Ca^{+2}$ were added to 25 to 100 mL of propylene glycol (PG) containing 0.005 M acetate buffer (90/10, sodium acetate/glacial acetic acid) vehicle with constant stirring at 60° C.±5° C. Following dissolution, glycerol was then added to produce the non-aqueous formulation.

1.4 Calcium and/or Magnesium Additions Using Stock Solutions 1.4.1 Initial Studies Stock solutions of calcium acetate, magnesium acetate alone and a mixture of both were prepared in propylene glycol (25.4 μg $Ca^{+2}$/g, 28.0 μg $Mg^{+2}$/g and 14.0 μg $Ca^{+2}$/g with 12.7 μg $Mg^{+2}$/g respectively). The individual stock solutions were added in aliquots up to a total of 1 mL in 33 mL of propylene glycol containing lipid blend (15 mg/mL). The solutions were compared to propylene glycol alone, and the solution first showing cloudiness recorded.

1.4.2 Follow-Up Studies with Reference Scale

Stock solutions of calcium acetate, monohydrate were prepared in propylene glycol (299 $Ca^{+2}$ μg/g), propylene glycol and glycerol (299 $Ca^{+2}$ μg/g), or water (6085 $Ca^{+2}$ μg/g) and vehicle matched when added to the propylene glycol, the non-aqueous phospholipid concentrate or the aqueous formulation (before or after addition of the non-aqueous phospholipid concentrate). The maximum added calcium stock was always <12% of the total volume.

Some non-aqueous phospholipid concentrates were titrated with calcium acetate. The appearance was evaluated on a 0, +, ++, +++ scale by visual inspection. FIG. 1 provides the scale used for the determinations, and was generated using low $Ca^{+2}$ lipids (DPPC, DPPA and MPEG5000-DPPE; 0.401:0.045:0.304 [wt:wt:wt]) formulated in propylene glycol at 15 mg total lipid/mL.

1.5 Filtration:

1.5.1 Aqueous Formulation

Prepared samples of phospholipid aqueous suspensions were held at 55° C. prior to filtration. Samples were placed in a 55° C. temperature controlled 60 mL syringe with a 13 mm Hydrophilic Polyvinylidene Fluoride (PVDF) 0.22 μm membrane syringe filter attached. A 5 psi nitrogen head pressure was applied to the syringe. Flow rate was determined by weighing the filtered solution over time with readings every 30 seconds. Flow rates per time point were calculated and the average flow between 9 to 10 minutes was compared to the initial flow (0 to 1 minute) and expressed as a percentage. A pre-filtration sample was collected along with samples throughout the filtration for phospholipid concentration analysis.

1.5.2 Non-Aqueous Formulation

Prepared samples of phospholipid non-aqueous solutions were held at 60° C. prior to filtration. Samples were placed in a 60° C. temperature controlled 60 mL syringe with 25 mm Hydrophilic Polyethersulfone (PES) 0.2 µm membrane syringe filter attached. A 10 psi nitrogen head pressure was applied to the syringe. Flow rate was determined by weighing the filtered solution over time with readings every 30 seconds. Flow rates per time point were calculated and the average flow between 8 to 9 minutes was compared to the initial flow (0 to 1 minute) and expressed as a percentage. Flow rates in clear solutions were seen to increase with time as the filter warmed. Samples were collected as outlined above.

1.6 Phospholipid Assay:

In some cases samples were assayed for phospholipid content. The sample was transferred to a HPLC vial and analyzed by reverse phase HPLC separation and Corona Charged aerosol detection (CAD; HPLC With Charged Aerosol Detection for the Measurement of Different Lipid Classes, I. N. Acworth, P. H. Gamache, R. McCarthy and D. Asa, ESA Biosciences Inc., Chelmsford, Mass., USA; J. Waraska and I. N. Acworth, American Biotechnology Laboratory, January 2008) and quantified versus reference standards.

1.7 Product Preparation and Testing

1.7.1 Aqueous Formulation

Filtered aqueous formulation (see section 1.5.1) was aliquoted (1.76 mL) into 2 cc Wheaton vials the headspace air replaced with perfluoropropane (PFP) gas, the vial sealed with a West grey butyl stopper, and crimped with an aluminum seal.

1.7.2 Non-Aqueous Formulation

Filtered aqueous formulation (see section 1.5.2) was aliquoted (0.35 mL) into 2 cc Wheaton vials the headspace air replaced with perfluoropropane (PFP) gas, the vial sealed with a West grey butyl stopper, and crimped with an aluminum seal.

1.7.3 Sysmex Microsphere Sizing:

Samples were analyzed for number and size distribution using a particle sizer (Malvern FPIA-3000 Sysmex). Aqueous or non-aqueous samples were optimally activated using a VIALMIX®, a portion of the activated product diluted with saline and then transferred to the sample vessel of the Sysmex. The Sysmex uses an appropriate sheath solution and analyzes the sample using both low and high power fields to generate sizing data for the specified size range (1 to 80 µm in the current studies).

1.7.4 Ultrasound Contrast of Activated Product:

Acoustic attenuation was measured for selected samples using a Philips Sonos 5500 clinical ultrasound imaging system. Following optimal activation with a VIALMIX® 10 microliter samples were pipetted into a 250 mL beaker containing 200 ml of 0.9% saline at room temperature. A round, vaned, 38 mm diameter stirring bar maintained solution uniformity and served as an acoustic reflector. The s3 clinical transducer of the ultrasound system was positioned at the top of the beaker, just into the solution and 4.8 cm above the upper margin of the stirring bar. Five seconds of 120 Hz images were then acquired digitally and written to disk beginning 10 seconds after introduction of the sample. The US system was used in IBS mode, TGC was fixed at the minimal value for all depths, and LGC was disabled. The mechanical index (MI) was 0.2 with power set 18 dB below maximum. The receive gain was fixed at 90 and the compression at 0. For each sample tested, US data acquisition was acquired prior to (blank) and after sample injection.

Image analysis was performed using Philips QLab version 2.0, which read files produced by the US system and calculated values in dB for IBS mode. Regions of interest were drawn on the stirring bar and the dB values exported to Excel. These were then averaged over the full 5 second (approximately 360 video frame) acquisition. Attenuation measurements were obtained by subtracting the averaged sample ROI value from the averaged blank ROI value (both in dB). This was divided by twice the distance between the US transducer and the upper margin of the stirring bar to yield attenuation in dB/cm. Values were then divided by the calculated microbubble concentration in the beaker and expressed in terms of dB attenuation per centimeter per million microbubbles/mL.

Example 1: Effect of Calcium Addition to Non-Aqueous Phospholipid Solution

This example demonstrates the effect of calcium and magnesium ions on phospholipid precipitation.

Example 1.1: Initial Studies on the Effect of Calcium and Magnesium Addition to Non-Aqueous Solution In initial studies, lipid blend (LB, Lot 1) characterized as having low divalent metal ion concentration (Table 1 in example methods), was added to propylene glycol at 55°±5° C. and stirred. It was verified by visual observation that the phospholipids had fully dissolved and the resulting solution was clear. This LB solution was titrated with calcium (25.4 µg $Ca^{+2}$/g), magnesium (28.0 µg $Mg^{+2}$/g) or a combination (1:1 to make a solution containing 14.0 µg $Ca^{+2}$/g and 12.7 µg $Mg^{+2}$/g) and showed cloudiness at 3.60 µg $Ca^{+2}$/g, 4.23 µg $Mg^{+2}$/g and 2.35 µg/g combined metal ion/g non-aqueous phospholipid solution, respectively.

Figure 2:
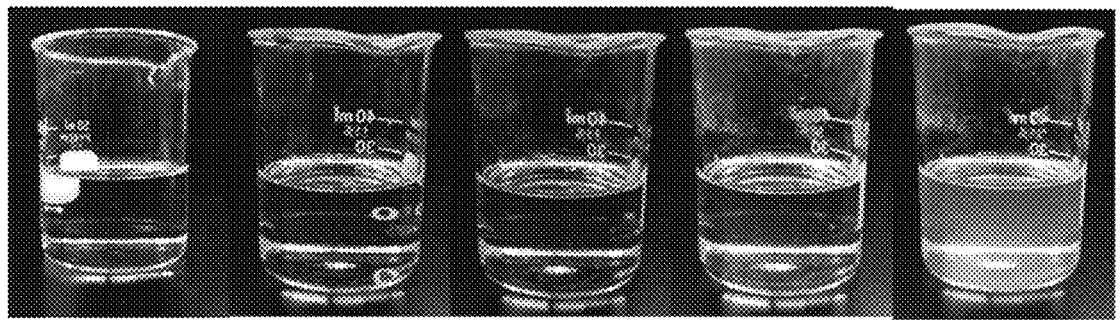
FIG. 2 is a photograph showing the appearance of solution upon successive additions of DPPC, MPEG5000-DPPE, DPPA, and calcium acetate.

Example 1.2: Follow-Up Studies on the Effect of Calcium Addition to Non-Aqueous Solution The experiment was conducted as follows: DPPC, DPPA and MPEG5000-DPPE powder, characterized as having low divalent metal ion concentration (Table 1 in example methods), were added either individually (in the sequence shown in Table 2) or as a mixture or as a blend added to heated (55° C.±5° C.) and stirred propylene glycol (PG) or a 1:1 mixture of propylene glycol and glycerol (PG/G). It was verified by visual observation that the phospholipids had fully dissolved and the resulting solution was clear (=0: see example methods Section 1.4.2, FIG. 1 for rating scale). FIG. 2 illustrates the appearance of a lipid concentrate in propylene glycol upon the successive additions of DPPC, MPEG5000-DPPE, DPPA and calcium acetate stock (1 mL of a 299 µg $Ca^{+2}$ per mL of stock was added to produce a lipid concentrate with an 11.1 µg $Ca^{+2}$ per g of solution). The lipid concentrate did not turn cloudy until the calcium was added.

Figure 3:
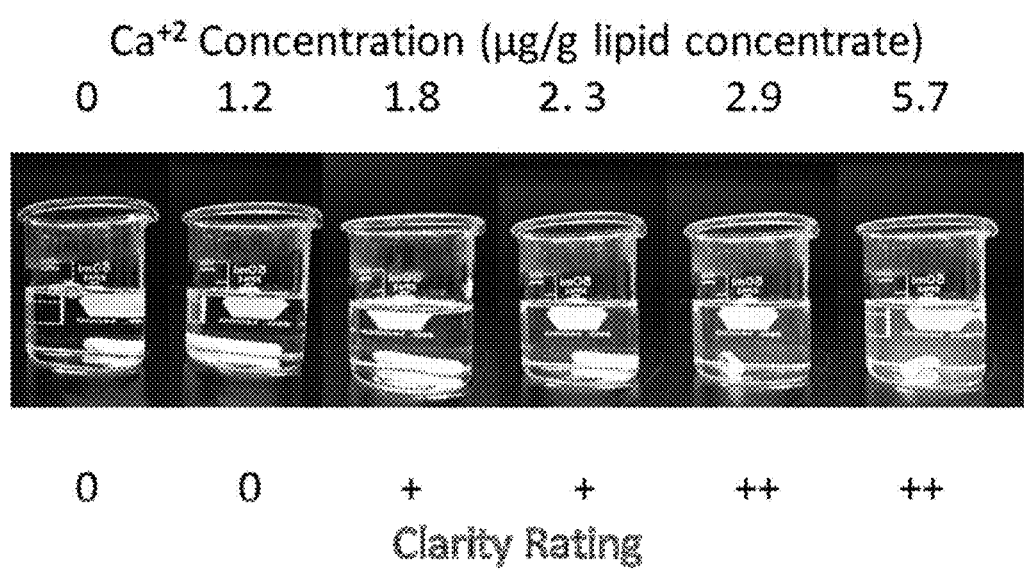
FIG. 3 is a photograph showing the appearance of titrated solutions for Study 4 as described in the Examples.

Phospholipid solutions in PG or 1:1 mixture PG/G were titrated by a series of small additions of calcium. After each addition, the solution was assessed for clarity (see example methods Section 1.4.2, FIG. 1 for rating scale) and the lowest calcium concentration producing a +, ++, and +++ score is shown in Table 2. FIG. 3 shows representative solutions for the Study 4 titration.

TABLE 2

Effect of Calcium addition to Non-aqueous phospholipid solution

| | Order of lipid addition | | | Non-aqueous Solvent | Observed cloudiness thresholds (µg Ca$^{+2}$/g) for with calcium [a,b] | | |
|---|---|---|---|---|---|---|---|
| Study | DPPC | MPEG5000-DPPE | DPPA | | + | ++ | +++ |
| 1 [c] | 1 | 3 | 2 | PG | 1.5 | 2.6 | >5.7 |
| 2 [c] | 2 | 3 | 1 | PG | 1.5 | 2.9 | >11.1 |
| 3 [c] | 3 | 1 | 2 | PG | 2.3 | 4.6 | 11.1 |
| 4 [c] | 1 | 2 | 3 | PG | 1.8 | 2.9 | >5.7 |
| 5 [d] | | phospholipid Blend | | PG | 1.8 | 5.7 | 11.1 |
| 6 [e] | | phospholipid Mixture (dry) | | PG | 1.8 | 5.7 | 11.1 |
| 7 [f] | 1 | 3 | 2 | PG & G | Lipids not dissolved | | |
| 8 [g] | 1 | 3 | 2 | PG & G | 2.6 | 19.2 | 35.8 |

[a] Defined in methods Section 1.4
[b] Titrated with calcium acetate stock solutions (299 µg Ca$^{+2}$/g of stock solution)
[c] DPPA (0.9 mg/mL), DPPC (8.02 mg/mL) and MPEG5000-DPPE (6.08 mg/mL) final concentration was achieved by individual phospholipid addition to propylene glycol (25 mL)
[d] Phospholipid blend (15 mg/mL), made using methanol to dissolve phospholipids at 55° C. followed by drying, dissolved in 25 mL propylene glycol
[e] Phospholipid mixture: DPPA, DPPC, and MPEG5000-DPPE (0.045:0.401:0.304), powders were stirred together and used for compounding in 25 mL propylene glycol. The final concentration is 15 mg/mL
[f] Phospholipid solution made by adding individual phospholipids [DPPA (0.9 mg/mL), DPPC (8.02 mg/mL) and MPEG5000-DPPE (6.08 mg/mL)] to 25 mL, 1:1 (v/v) propylene glycol:glycerol
[g] Phospholipid solution made by adding individual phospholipids [DPPA (0.225 mg/mL), DPPC (2.00 mg/mL) and MPEG5000-DPPE (1.70 mg/mL)] to 100 mL, 1:1 (v/v) propylene glycol:glycerol Calcium titration produced a clear concentration dependent precipitation in the phospholipid solution irrespective of the how the phospholipids were added (individually, as a mixture or as a blend) to the propylene glycol (see Table 2). The lipids were not soluble in either glycerol alone or in 25 mL of 1:1 PG/G but did achieve a clear solution when added to 100 mL of 1:1 PG/G (Study 8). Calcium produced a concentration dependent precipitation in this lipid solution consistent with initial findings (see Table 2). Overall, these titration studies indicated the lowest calcium, magnesium and combined concentrations that produced precipitation was 1.5 µg Ca$^{+2}$/g, 4.23 µg Mg$^{+2}$/g, and 2.35 µg combined metal ion/g non-aqueous phospholipid solution.

Example 2: Effect of Phospholipid Solution Components Containing Calcium when Mixed

Example 2.1: Calcium in PG

Study 9 was conducted as follows: DPPC, MPEG5000-DPPE and DPPA powder, characterized as having low calcium concentration (see Table 1 in example methods), were added individually (in the sequence shown in Table 3) to heated (55° C.±5° C.) and stirred PG containing 11 µg/g calcium. Clarity was assessed (see Section 1.4) and the solution was clear after DPPC dissolved, turned and stayed cloudy after addition of DPPA, and remained cloudy after addition of MPEG5000-DPPE. The cloudiness observed was scored as +++ (FIG. 1, Section 1.4). This contrasted with the clear solution produced when these phospholipids (including DPPA) were added to PG containing low calcium (starting solution for Study 1). This was further emphasized by Study 12, where only phospholipids DPPC and MPEG5000-DPPE containing high Ca$^{+2}$ levels, were dissolved and this solution stayed clear even with the presence of calcium.

Example 2.2: Calcium in Lipid Blend from MPEG5000-DPPE

Initial experiments were performed on phospholipid blend (made using toluene and methanol to dissolve and adding MTBE to precipitate out the lipid blend) containing DPPC, DPPA and either low (not detected Ca$^{+2}$ and 1 µg Mg$^{+2}$/g, MPEG5000-DPPE) or high (980 µg Ca$^{+2}$/g and 150 µg Mg$^{+2}$/g, MPEG5000-DPPE Lot 1) calcium and magnesium containing MPEG5000-DPPE, respectively, were added to heated (55° C.±5° C.) and stirred propylene glycol. The two lipid blends were mixed to provide samples having approximately 0, 1.75, 4.11 and 12.9 µg combined Ca$^{+2}$ & Mg$^{+2}$/g of non-aqueous phospholipid solution. The 1.75 µg combined Ca$^{+2}$ & Mg$^{+2}$/g of non-aqueous phospholipid solution showed cloudiness.

Follow-up study 10 and 11 were conducted as follows: phospholipid blend (made using toluene and methanol to dissolve and adding MTBE to precipitate out the phospholipid blend) containing DPPC, DPPA and either high (980 ppm Ca$^{+2}$, 150 ppm Mg$^{+2}$, Lot 1) or low (4 ppm Ca$^{+2}$) calcium containing MPEG5000-DPPE were added to heated (55° C.±5° C.) and stirred PG. Clarity was assessed (see Section 1.4) and slight cloudiness was observed (+; see example methods in Section 1.4, Error! Reference source not found.) with the phospholipid blend containing high calcium (measured as 370 ppm Ca$^{+2}$ and 54 ppm Mg$^{+2}$). This contrasted with the clear solution produced by dissolving low calcium (non-detectable levels of Ca$^{+2}$ and Mg$^{+2}$) containing phospholipid blend (see Table 3).

TABLE 3

Effect of Phospholipid solution components containing calcium when mixed

| | Order of phospholipid addition | | | Non-aqueous Solvent | Ca$^{+2}$ (Mg$^{+2}$) µg/g [source] | Observed Cloudiness Level [a] |
|---|---|---|---|---|---|---|
| Study | DPPC | MPEG5000-DPPE | DPPA | | | |
| 9 [b] | 1 | 2 | 3 | PG | 11.2 (0.0) [added to PG before lipid addition] | +++ [c] |
| 12 [d] | 1 | 2 | — | PG | 5.8 (0.9) [High Ca$^{+2}$ MPEG-5000-DPPE] | 0 [e] |
| 10 | | Phospholipid blend containing low Ca$^{+2}$ [f] | | PG | 0.0 (0.0) [LB Lot 1] | 0 |
| 11 | | Phospholipid blend containing high Ca$^{+2}$ [f] | | PG | 5.36 (0.8) [LB Lot 2] | +++ |

[a] Defined in methods Section 1.4
[b] DPPA (0.9 mg/mL), DPPC (8.02 mg/mL) and MPEG5000-DPPE (6.08 mg/mL) final concentration was achieved by individual phospholipid addition to propylene glycol (25 mL)
[c] Solution was clear when DPPC solubilized, remained clear after addition of MPEG5000-DPPE turned cloudy after addition of DPPA
[d] DPPC (8.02 mg/mL) and MPEG5000-DPPE containing Ca$^{+2}$ (6.08 mg/mL; 980 ppm Ca$^{+2}$ and 150 ppm Mg$^{+2}$); final concentration was achieved by individual phospholipid addition to propylene glycol (25 mL), no DPPA added
[e] Solution was clear upon addition of DPPC and MPEG5000-DPPE
[f] Phospholipid blend (15 mg/mL) made using toluene and methanol to dissolve phospholipids and adding MTBE to precipitate out the phospholipid blend, dissolved in 25 mL propylene glycol

Example 2.3: Calcium from MPEG5000-DPPE Added Individually

Figure 4:
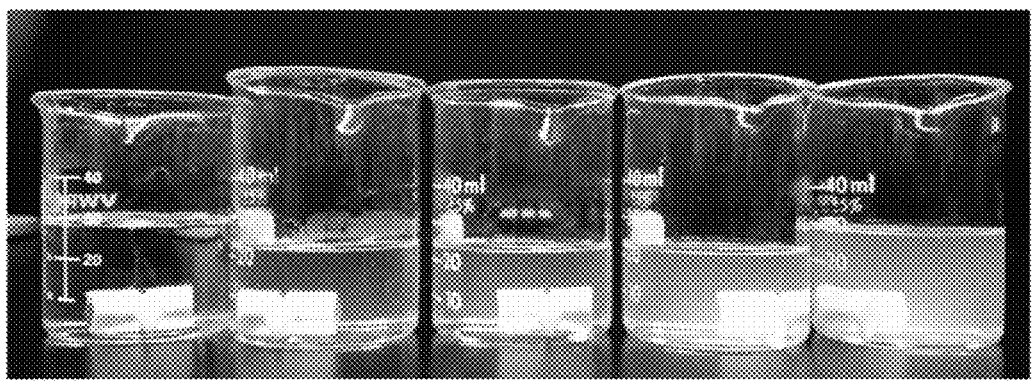
FIG. 4 is a photograph showing the appearance of solutions prepared with different proportions of MPEG5000-DPPE and MPEG5000-DPPE containing high calcium (Ca+2) levels.

Studies 13 through 17 were conducted as follows: DPPA and DPPC, characterized as having low calcium concentration (see Table 1 in example methods), were added individually (in the sequence shown in Table 4) to heated (55° C.±5° C.) and stirred PG. MPEG5000-DPPE containing different proportions of "low" and "high" calcium and magnesium material was added. Clarity was assessed (see example methods in Section 1.4, FIG. 1) and a calcium and magnesium concentration dependent precipitation was observed (see Table 4 and FIG. 4).

TABLE 4

Calcium and Magnesium from MPEG5000-DPPE added as an individual component

| | Order of lipid addition | | Percentage [c] | | | Metal ion | | | |
|---|---|---|---|---|---|---|---|---|---|
| | | | MPEG5000-DPPE | MPEG5000-DPPE | Non-aqueous | Concentration (μg/g) | | | Observed Cloudiness |
| Study | DPPC | DPPA | (Low Ca$^{+2}$) | (high Ca$^{+2}$) | Solvent | Ca$^{+2}$ | Mg$^{+2}$ | Total | Level [a] |
| 13 [b] | 1 | 2 | 100 | 0 | PG | 0.1 | 0.0 | 0.1 | 0 |
| 14 [b] | 1 | 2 | 75 | 25 | PG | 0.7 | 0.1 | 0.8 | + |
| 15 [b] | 1 | 2 | 50 | 50 | PG | 1.3 | 0.3 | 1.6 | ++ |
| 16 [b] | 1 | 2 | 25 | 75 | PG | 1.9 | 0.4 | 2.3 | ++ |
| 17 [b] | 1 | 2 | 0 | 100 | PG | 3.1 | 0.6 | 3.7 | +++ |
| 18 | 1 | 2 | n/p [d] | n/p [d] | PG & G [e] | Not added | | | Cloudy, DPPA not dissolved |

[a] Defined in methods Section 1.4
[b] DPPA (0.9 mg/mL), DPPC (8.02 mg/mL) and MPEG5000-DPPE (6.08 mg/mL) final concentration was achieved by individual phospholipid addition to propylene glycol (25 mL)
[c] Percentages of MPEG5000-DPPE; low Ca$^{+2}$ [4 ppm] and high Ca$^{+2}$ [520 ppm Ca$^{+2}$, 110 ppm Mg$^{+2}$] relative to total
[d] n/p = not performed; Phospholipids [DPPC (8.02 mg/mL) and DPPA (0.9 mg/mL)] not solubilized in propylene & glycol solvent system
[e] Propylene glycol and glycerol 50:50 (v/v)

Summary of Example 2

Overall these studies have demonstrated the addition of calcium, either in the non-aqueous solvent or via the phospholipid blend or when added as MPEG5000-DPPE as an individual compound, all caused precipitation. The concentration where effects were seen were similar for Example 2 compared to those in Example 1. The lowest calcium concentration that produced cloudiness (+) was at 0.7 μg/g Ca$^{+2}$ (0.8 μg/g total Ca$^{+2}$ and Mg$^{+2}$). This is a similar concentration to the 1.5 to 2.6 μg/g seen in Example 1.

Example 3: Addition of Non-Aqueous Phospholipid Solution to Aqueous Solvent

Example 3.1: Effect of Calcium in Non-Aqueous Phospholipid Solution on Addition to Aqueous Solvent A series of studies were performed to examine the impact of calcium in the non-aqueous phospholipid solution prior to transferring into the aqueous formulation. These involved the steps of: 1) preparing a non-aqueous phospholipid solution, 2) preparing an aqueous solution and 3) combining solutions from 1 and 2.

Example 3.1.1: Preparing Non-Aqueous Solution: Calcium Added to Non-Aqueous Solution after Phospholipids Dissolved Consistent with Example 2, the first step in studies 19, 20 and 22 were as follows: DPPC, DPPA, and MPEG5000-DPPE powder, characterized as having low calcium concentration (see Table 1 in example methods), were added individually (in the sequence shown in Table 5) to heated (55° C.±5° C., with the exception of study 22, which was heated to 70° C.) and stirred propylene glycol. It was verified by visual observation that the phospholipids had fully dissolved and the resulting solution was clear (see example methods in Section 1.4, FIG. 1). A solution of calcium acetate [Ca(OAc)$_2$] in propylene glycol was added as indicated in Table 5, the solution was stirred and observed for changes in appearance, as compared to a solvent blank and the assessment of clarity was recorded. Upon addition of calcium acetate, the solutions turned cloudy. These propylene glycol concentrates were transferred to the aqueous phase as described below.

Example 3.1.2 Preparing Non-Aqueous Solution: Calcium in MPEG5000-DPPE

The first step studies 21 and 25 were as follows: DPPC, DPPA (not included in study 25), and calcium containing MPEG5000-DPPE powder (980 ppm, MPEG5000-DPPE Lot 1; see Table 1 in example methods), were added individually (in the sequence shown in Table 5) to heated (55° C.±5° C.) and stirred in PG. Clarity was assessed and significant cloudiness observed in study 21 (+++; see example methods in Section 1.4, FIG. 1) after addition of DPPA, and remained cloudy after addition of MPEG5000-DPPE, whereas no cloudiness was observed in study 25 which did not contain DPPA. These non-aqueous phospholipid solutions were transferred to the aqueous phase as described below.

Example 3.1.3: Preparing Non-Aqueous Solution: Calcium in Lipid Blend from MPEG5000-DPPE Consistent with Example 2, the first step in studies 23 and 24 were conducted as follows: phospholipid blend (made using toluene and methanol to dissolve and adding MTBE to precipitate out the lipid blend) containing DPPC, DPPA and either low (4 ppm, lot 2 or high (980 ppm, MPEG5000-DPPE Lot 1) calcium containing MPEG5000-DPPE, respectively, were added to heated (55° C.±5° C.) and stirred propylene glycol. Clarity was assessed and significant cloudiness observed (+++; see example methods in Section 1.4, FIG. 1) with the phospholipid blend containing high calcium. This contrasted with the clear solution produced by dissolving low calcium containing phospholipid blend (see Table 5). These non-aqueous phospholipid solutions were transferred to the aqueous phase as described below.

Example 3.1.4: Preparing Non-Aqueous Solution: Calcium in PG Prior to Adding Phospholipids Consistent with Example 2, the first step in studies 28 and 30 were conducted as follows: DPPC, MPEG5000-DPPE and DPPA powder, characterized as having low calcium concentration (see Table 1 in example methods), were added individually (in the sequence shown in Table 5) to heated (55° C.±5° C.) and stirred PG either containing 11 μg/g calcium or calcium added after phospholipid addition, respectively. Clarity was assessed (see example methods in Section 1.4, FIG. 1) and in study 28 the solution was clear after DPPC and MPEG5000-DPPE dissolved but turned and stayed cloudy after addition of DPPA. In study 30 the solution was clear after DPPC, DPPA and MPEG5000-DPPE were dissolved, and turned cloudy after addition of $Ca^{+2}$. The cloudiness for both studies was scored as +++ (see Table 5). These non-aqueous phospholipid solutions were transferred to the aqueous phase as described below.

Example 3.2: Preparing Aqueous Solution

For all studies the aqueous solution was prepared as follows: In a separate vessel Sodium Chloride (NaCl), Sodium Phosphate Dibasic Heptahydrate ($Na_2HPO_4.7H_2O$), and Sodium Phosphate Monobasic ($NaH_2PO_4.H_2O$) were added to water in a stirred vessel, and mixed until dissolved. Propylene glycol and glycerol were also added, as needed, so the final addition of phospholipid concentrate will reconstitute to an 8:1:1 water:glycerol:propylene glycol composition. This stirred solution was maintained at 55° C.±5° C. (with the exception of study 22 where the aqueous solution was maintained at 70° C.).

Example 3.3: Combining Non-Aqueous and Aqueous Solutions

For all studies, the addition of the non-aqueous phospholipid concentrate to the aqueous solution was done as follows: The warm phospholipids in propylene glycol were added and stirred at 100 to 150 rpm. Visual observations were recorded and the time for full dispersion or dissolution was (either clear or cloudy) noted. These aqueous suspensions were then collected and filtered through a 0.2 um filter at 55° C. under 5 psi head pressure. Flow rate was measured and samples collected for phospholipid measurement (see example methods for procedure). Pre- and post-filtration samples were assayed to determine the level of phospholipid loss associated with filtration.

TABLE 5

Effect of divalent metal ion in non-aqueous phospholipid solution on addition to aqueous solvent

| | Non-aqueous phospholipid concentrate [a] | | | | Aqueous suspension [b] | | Percent of Initial | | |
|---|---|---|---|---|---|---|---|---|---|
| Study | Phospholipid addition to PG | $Ca^{+2}$ ($Mg^{+2}$) μg/g PG [$Ca^{+2}$ source] | Observed cloudiness [c] | Contains phosphate buffer | Appearance after addition to aqueous | $Ca^{+2}$ ($Mg^{+2}$) concentration in aqueous [μg/g water] | Filtration Rate at 9 to 10 minutes | % phospholipid post filtration [d] | |
| | | | | | | | | DPPC  PDDA | MPEG5000-DPPE |
| 19 | C, E, A | 0.0 (0.0) | 0 | Yes | Clear | 0 (0) | 64.6 | 101  100 | 99 |
| 20 | C, E, A | 13.7 (0)[e] [Calcium acetate added after lipids] | +++ | Yes | Cloudy | 0.8 (0) | 1.3; blocked filter | 95  76 | 94 |
| 21 | C, A, E | 3.1 (0.7)[f] [in MPEG5000-DPPE] | +++ | Yes | Cloudy | 0.2 (0.03) | 9.0; blocked filter | 96  78 | 95 |
| 22 [g] | C, A, E | 21.4 (0)[e] [Calcium acetate added after lipids] | +++ | Yes; at 70° C. | Cloudy | 1.2 (0) | 8.5; blocked filter | 98  75 | 97 |
| 25 | C, E | 5.8 (0.9)[h] [in MPEG5000-DPPE] | 0 | Yes | Clear | 0.3 (0.04) | 82.1 | 100  nd | 99 |
| 23 | LB [i] | 0 (0) | 0 | Yes | Clear | 0 (0) | 92.0 | 99  100 | 99 |
| 24 | LB [i] | 5.36 (0.8) [Lipid Blend] | +++ | Yes | Slightly cloudy | 0.3 (0.04) | 5.2 blocked filter | 98  65 | 96 |
| 28 | C, E, A | 11.2 (0.0)[k] [Calcium acetate in PG, then phospholipid added] | +++ | Yes | Cloudy | 0.6 (0) | 42.7 | 101  24 | 100 |
| 30 | C, A, E | 21.4 (0.0)[e] [Calcium acetate added after lipids] | +++ | No | Cloudy | 1.2 (0) | 9.0 blocked filter | 89  42 | 86 |

[a] Phospholipid concentrate was prepared at 15 mg/mL by dissolving DPPC (C), MPEG5000-DPPE (E) and DPPA (A) in the ratio of 0.401:0.304:0.045 in propylene glycol in the order listed at 55° C.
[b] Phospholipid concentrates were added to a compounding vessel containing: water (800 mg); dibasic sodium phosphate, heptahydrate (2.16 mg); monobasic sodium phosphate, monohydrate (2.34 mg); sodium chloride (4.84 mg), glycerol (126 mg), and propylene glycol (51.75 mg) per mL of compounding solution. Materials were combined at 55° C., in the order listed.
[c] Defined in methods Section 1.4.2

TABLE 5-continued

Effect of divalent metal ion in non-aqueous phospholipid solution on addition to aqueous solvent

| | Non-aqueous phospholipid concentrate [a] | | | Aqueous suspension [b] | | | | Percent of Initial | |
|---|---|---|---|---|---|---|---|---|---|
| Study | Phospholipid addition to PG | $Ca^{+2}$ ($Mg^{+2}$) µg/g PG [$Ca^{+2}$ source] | Observed cloudiness [c] | Contains phosphate buffer | Appearance after addition to aqueous | $Ca^{+2}$ ($Mg^{+2}$) concentration in aqueous [µg/g water] | Filtration Rate at 9 to 10 minutes | % phospholipid post filtration [d] | |
| | | | | | | | | DPPC  PDDA | MPEG5000-DPPE |

Figure 5:
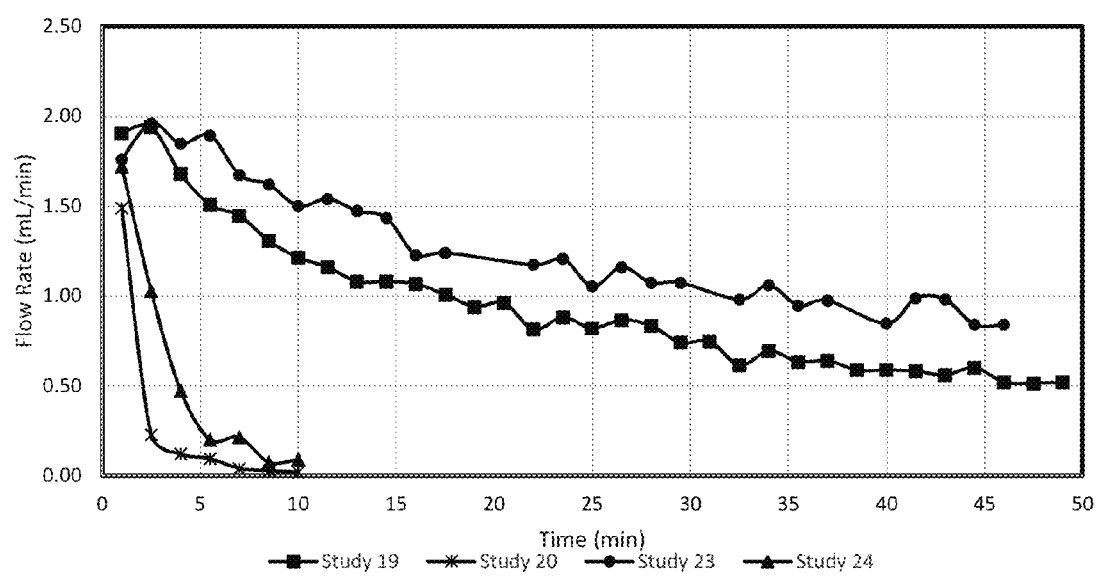
FIG. 5 is a graph showing filtration flow rate for phospholipid aqueous formulation made with individual phospholipids or phospholipid blend containing either high or low calcium. Studies 19 and 23 were made with low calcium components whereas studies 20 and 24 contain high calcium levels (see Table 6 for details). Each graphed point is an average of three consecutive filtration rate measurements with corresponding time within each study.

[d] HPLC with CAD detection described in Section 1.6
[e] 1 mL, 2 mL and 2 mL (Study 20, 22, and 30, respectively) of a stock 299 µg $Ca^{+2}$ per g PG, after lipid addition prior to transfer to the aqueous compounding solution
[f] MPEG5000-DPPE containing $Ca^{+2}$ (6.08 mg/mL; 520 and 110 ppm $Ca^{+2}$ and $Mg^{+2}$) used for experiment
[g] All compounding performed at 70° C.
[h] MPEG5000-DPPE containing $Ca^{+2}$ (6.08 mg/mL; 980 and 150 ppm $Ca^{+2}$ and $Mg^{+2}$) used for experiment
[i] Made using toluene and methanol to dissolve lipids and adding MTBE to precipitate out the lipid blend. Resulting lipid blend added to 25 mL propylene glycol (15 mg/mL). Study 23 used low $Ca^{+2}$ lipid blend and Study 24 used lipid blend containing $Ca^{+2}$ and $Mg^{+2}$ (370 and 54 µg/g, respectively).
[k] Added 1 mL of a stock 299 µg $Ca^{+2}$ per g PG, prior to addition of lipids Consistent with the previous examples, these studies showed precipitation occurred in the non-aqueous phospholipid solution when high calcium or calcium and magnesium were present. This occurred regardless of if the calcium was present in the propylene glycol prior to the phospholipid addition, added after the phospholipid addition or added with one of the components of the phospholipids (either with MPG5000 DPPE or in a phospholipid blend). Once the precipitate was formed it did not disperse when mixed with aqueous solvent. This resulted in a cloudy aqueous preparation that had a reduced rate of filtration initially and often blocked the 0.2 µm filter (Table 5; FIG. 5). The filtrate of cloudy aqueous preparations was clear but phospholipid measurement indicated consistently reduced levels of DPPA. This effect was apparent for both individually added phospholipids and phospholipids added as a blend.

Example 3.4: Effect of Non-Aqueous Phospholipid Solution Addition to Aqueous Solvent Containing Calcium A series of studies were performed to examine the impact of calcium in the aqueous solution on phospholipid suspension preparation. These involved the steps of: 1) preparing a non-aqueous phospholipid solution, 2) preparing an aqueous solution and 3) combining solutions from 1 and 2.

Example 3.4.1: Preparing Non-Aqueous Solution

Consistent with Example 1, the first step in Studies 26, 27 and 29 were conducted as follows: DPPC, DPPA and MPEG5000-DPPE powder, characterized as having low calcium concentration (see Table 1 in example methods), were added individually (in the sequence shown in Table 6) to heated (55° C.±5° C.) and stirred propylene glycol. It was verified by visual observation that the phospholipid had fully dissolved and the resulting solution was clear. These propylene glycol concentrates were transferred to the aqueous phase as described below.

Example 3.4.2: Preparing Aqueous Solution

In a separate vessel Sodium Chloride (NaCl), Sodium Phosphate Dibasic Heptahydrate ($Na_2HPO_4 \cdot 7H_2O$), and Sodium Phosphate Monobasic ($NaH_2PO_4 \cdot H_2O$) were added to water in a stirred vessel, and mixed until dissolved (for study 29 the Phosphate salts were excluded from the formulation). Propylene glycol and glycerol were also added as needed, so the final addition of non-aqueous phospholipid solution will reconstitute an 8:1:1 water:glycerol:propylene glycol composition. In some studies, a solution of calcium acetate [$Ca(OAc)_2$] in water was added as indicated in Table 6. This aqueous solution was stirred, maintained at 55° C.±5° C. It was identified that the addition of 48.4 µg/g calcium caused a marked flocculation in the aqueous solution in the absence of any phospholipids (see Table 6, study A). At 12.2 µg/g calcium no precipitation was produced in the aqueous solution (see Table 6, study B).

Example 3.4.3: Combining Non-Aqueous and Aqueous Solutions

For all studies, the addition of the non-aqueous phospholipid concentrate to the aqueous solution was done as follows: the warm phospholipid dissolved in propylene glycol was added and stirred at 100 to 150 rpm. Visual observations were recorded and the time for full dispersion or dissolution is stable (either clear or cloudy) noted. For study 27, the aqueous formulation was initially clear. Calcium was titrated and at concentrations ≥30.4 µg/g a cloudy precipitate was formed (see Table 6). It was noted, however, that the aqueous solution without phospholipid had a marked precipitated at 48.4 µg/g (Study A; Table 6). In study 27, at calcium levels where the aqueous solution alone was not effected (12.2 µg/g based on study B, Table 6), no effect was seen on aqueous Phospholipid formulation clarity. This was confirmed in study 26, where calcium was added to the aqueous solution (12.2 µg/g) prior to combining with the non-aqueous phospholipid concentrate. This was further extended in study 29, where the phosphate buffer was excluded from the aqueous solution. Initially, calcium was added to the aqueous solution (12.2 µg/g) prior to combining with the non-aqueous phospholipid concentrate and the formulation was clear. Additional calcium was added after the phospholipid addition to the formulation up to 96 µg/g and no precipitation was observed.

The aqueous formulations from study 26 and 29 were then collected and filtered through a 0.2 µm filter at 55° C. under 5 psi head pressure. Flow rate at 10 minutes was not reduced compared to initial flow; all the sample was filtered and overall filtration was similar to preparations not containing calcium (see studies 19, 23 and 25). Pre- and post-filtration samples were collected and compared to determine loss of phospholipids associated with filtration. No meaningful loss of Phospholipid was apparent (see Table 6).

TABLE 6

Effect of non-aqueous phospholipid solution addition to aqueous solvent containing divalent metal ions

| | Non-aqueous lipid concentrate | | Calcium concentration | Aqueous suspension [a] | | | | | |
|---|---|---|---|---|---|---|---|---|---|
| | | | | Appearance after lipid concentrate | Contains | Percent of Initial Filtration | % phospholipid post filtration [d] | | |
| Study | Phospholipid addition to PG[b] | Observed cloudiness [c] | in aqueous (µg $Ca^{+2}$/g) | addition to aqueous | $PO_4$ buffer | Rate at 9-10 minutes | DPPC | DPPA | MPEG5000-DPPE |
| 27 | C, E, A | 0 | Titration 0 to 48.7 µg $Ca^{+2}$/g | Clear to 12.2, slightly cloudy at 30.4 and cloudy with precipitate at 36.5 µg $Ca^{+2}$/g water | Yes | n/a | | | |
| 26 | C, E, A | 0 | 12.2 [e] | Clear | Yes | 114.3 | 99 | 101 | 98 |
| 29 | C, A, E | 0 | 12.2 [e] | Clear | No | 100.8 | 99 | 99 | 98 |
| A | n/a | n/a | 48.4 [e] | Precipitate | Yes | n/a | n/a | n/a | n/a |
| B | n/a | n/a | 12.2 [e] | Clear | Yes | n/a | n/a | n/a | n/a |

[a] All compounding performed at 55° C. Non-aqueous phospholipid solutions were added to aqueous compounding vessel containing: water (800 mg); sodium phosphate heptahydrate (2.16 mg/mL), sodium phosphate monohydrate (2.34 mg/mL), sodium chloride (4.84 mg/mL), glycerol (126 mg), and propylene glycol (51.75 mg) unless otherwise indicated in footnotes.
[b] "A" is DPPA (0.9 mg/mL), "C" is DPPC (8.02 mg/mL) and "E" is MPEG5000-DPPE (6.08 mg/mL) which were added in the order listed, to 25 mL propylene glycol
[c] Defined in methods Section 1.4
[d] HPLC with CAD detection described in Section 1.6
[e] Prior to addition of lipid concentrate to aqueous compounding vessel, 1 mL, 1 mL, 4 mL and 1 mL of calcium acetate concentrate (6.085 mg $Ca^{+2}$ per g of water) was added for studies 26, 29, A and B, respectively.

These studies demonstrate that calcium is not causing phospholipid precipitation in the aqueous formulation even up to 96 µg/g. However, at calcium levels higher than 12.2 µg/g the phosphate salts start to precipitate.

Example 4: Effect of Divalent Metal Ions on Phospholipid Dissolving in Buffered Propylene Glycol and with the Addition of Glycerol

Example 4.1: Calcium Titration in Buffered Non-Aqueous Phospholipid Concentrate Studies 31 and 32 were conducted as follows: DPPC, DPPA and MPEG5000-DPPE powder, characterized as having low calcium concentration (see Table 1 in example methods), were added either individually (in the sequence shown in Table 7) or as a phospholipid blend (made using toluene and methanol to dissolve and adding MTBE to precipitate out the lipid blend) to heated (55° C.±5° C.) and stirred acetate buffered propylene glycol. It was verified by visual observation that the lipid had fully dissolved and the resulting solution was clear (see example methods Section 1.4). A solution of calcium acetate [$Ca(OAc)_2$] in propylene glycol was used to titrate the phospholipid solution by a series of small additions. The solution was stirred and observed for changes in appearance during the titration, as compared to a solvent blank after each addition and the assessment of clarity was recorded. A cloudiness score (see Section 1.4, FIG. 1, for method) based on this assessment was made and the lowest calcium concentration producing a +, ++, and +++ score is shown in Table 7.

TABLE 7

Effect of calcium on phospholipid dissolving in buffered propylene glycol

| | Order of lipid addition [a] | | | Calcium | Observed cloudiness | | |
|---|---|---|---|---|---|---|---|
| | | | | Lipid | | thresholds (pg/mL $Ca^{+2}$) [b] | |
| Study | DPPC | DPPA | MPEG5000-DPPE | blend | concentration (µg/mL Ca+2) | + | ++ | +++ |
| 31 | n/a | n/a | n/a | 1 [c] | Titration [r] | 5.8 | 11.2 | 22.3 |
| 32 | 1 | 3 | 2 | n/a | Titration [s] | 11.3 | 17.0 | >33.5 |

[a] Individual lipids [DPPC (4.01 mg), DPPA (0.45 mg), and MPEG5000-DPPE (3.04 mg), in the order listed] or lipid blend (7.5 mg) were added to each mL of propylene glycol containing sodium acetate (0.74 mg) and acetic acid (0.06 mg), at 60° C. with stirring.
[b] Definedn methods Section 1.4
[c] Made using toluene and methanol to dissolve lipids and adding MTBE to precipitate out the lipid blend.

Example 4.2: Calcium Titration in Buffered Non-Aqueous Phospholipid Concentrate from MPEG5000-DPPE Studies 33 through 36 were conducted as follows: DPPC, DPPA and either high (980 ppm, Lot 1 or low $Ca^{+2}$ (4 ppm) containing MPEG5000-DPPE, were added individually (in the sequence shown in Table 8) or as a phospholipid blend (made using toluene and methanol to dissolve and adding MTBE to precipitate out the lipid blend) to heated (55° C.±5° C.) and stirred acetate buffered propylene glycol. Clarity was assessed (see example methods Section 1.4) and cloudiness was observed (+ or ++; see example methods, FIG. 1) with the phospholipid blend containing high calcium. This contrasted with the clear solution produced by dissolving low calcium containing phospholipid blend (see Table 8).

Example 4.3: Glycerol Addition

To these buffered non-aqueous phospholipid solutions, glycerol was transferred with stirring at 300 rpm. Many gas bubbles were trapped in the mixing solution but cleared once the stirrer was stopped. Visual observations were recorded and the clarity level (either clear or cloudy) noted. These PG/G solutions were then collected and filtered through a 0.2 µm filter at 60° C. under 10 psi head pressure. Flow rate was measured and samples collected for phospholipid measurement. Pre- and post-filtration samples were compared to determine loss of phospholipids associated with filtration.

These studies showed precipitation occurred in the buffered non-aqueous phospholipid solution in a calcium concentration dependent manner. This occurred regardless of whether the buffered non-aqueous phospholipid solution was made with individual phospholipids or a lipid blend and at concentrations that were not meaningfully different. The concentration to cause initial precipitation for the buffered solution was higher (5.8 to 11.3 µg/g $Ca^{+2}$) than for the non-buffered solutions (1.5-2.3 µg $Ca^{+2}$/g: see Table 2, studies 1 through 4) indicating an influence of the buffer.

Figure 6:
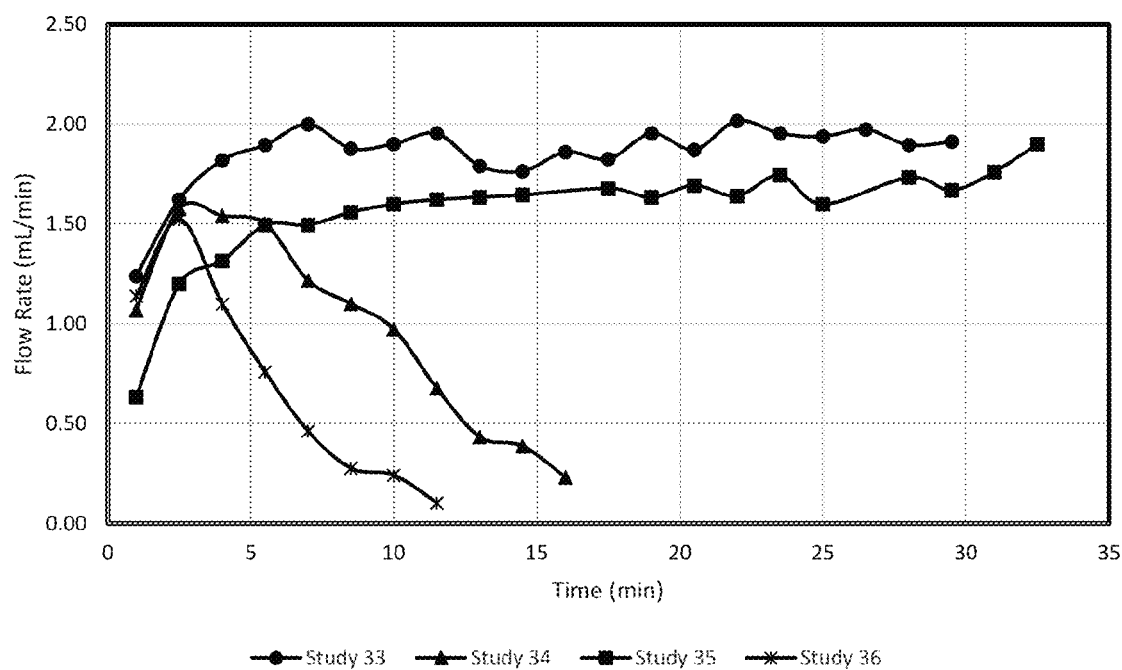
FIG. 6 is a graph showing filtration flow rate for phospholipid non-aqueous formulation made with individual phospholipids or phospholipid blend containing either high or low calcium. Studies 33 and 35 were made with low calcium components whereas studies 34 and 36 contain high calcium levels (see Table 9 for details). Each graphed point is an average of three consecutive filtration rate measurements with corresponding time within each study.

Calcium from the lipid blend caused precipitation in the buffered non-aqueous phospholipid solution as was seen in the non-buffered solution. Once the precipitate was formed it did not disperse when mixed with glycerol. This results in a cloudy non-aqueous formulation that had a reduced rate of filtration initially and often blocked the 0.2 µm filter (Table 8; FIG. 6). The filtrate of cloudy preparations was clear but phospholipid measurement indicated slightly reduced levels of DPPA.

Example 5: Microsphere Formation and Acoustic Detection of Manufactured Product

Example 5.1: Aqueous Phospholipid Suspension

Studies 37 and 38 were conducted as follows: filtered materials from study 19 and 23 were prepared in vials (see examples method Section 1.7.1). Following VIALMIX®, activation samples were analyzed for microsphere size and number (see methods Section 1.7.3) and clinical ultrasound acoustic attributes (see methods Section 1.7.4), see Table 9.

TABLE 8

Effect of Calcium on phospholipid dissolving in buffered propylene glycol and glycerol added

| | Acetate/Propylene glycol concentrate [a] | | | Propylene glycol with added glycerol [b] | | | | |
|---|---|---|---|---|---|---|---|---|
| Study | Lipid addition to PG | $Ca^{+2}$ ($Mg^{+2}$) [µg/g] | Observed cloudiness [c] | Appearance after addition of glycerol | $Ca^{+2}$ and ($Mg^{+2}$) concentration product [µg/g] | Percent of Initial Filtration Rate at 8-9 minute | % phospholipid post filtration [d] | |
| | | | | | | | DPPC DPPA | MPEG 5000 DPPE |
| 33 | LB [e] | 0 (0) | 0 | clear | 0 | 174.2 | 97   90 | 96 |
| 34 | LB [e] | 2.7 (0.4) | + | cloudy | 1.6 (0.2) | 96.7; blocked filter | 101   86 | 98 |
| 35 | C, A, E | 0 (0) | 0 | clear | 0 | 245.2 | 97   100 | 98 |
| 36 | C, A, E [f] | 2.9 (0.4) | ++ | cloudy | 1.7 (0.2) | 19.8; blocked filter | 99   80 | 100 |

[a] Individual lipids [DPPC (4.01 mg), DPPA (0.45 mg), and MPEG5000-DPPE (3.04 mg), in the order listed] or lipid blend (7.5 mg) were added to each mL of propylene glycol containing sodium acetate (0.74 mg) and acetic acid (0.06 mg), at 60° C. with stirring.
[b] Propylene glycol containing acetate buffer and phospholipids is diluted 1:1 (v/v) with glycerol.
[c] Defined in methods Section 1.4
[d] HPLC with CAD detection described in Section 1.6
[e] Lipid blend made using toluene and methanol to dissolve lipids and adding MTBE to precipitate out the lipid blend, low Ca+2 (Lot 1) for study 34, and high Ca+2 (370 $Ca^{+2}$ and 54 ppm $Mg^{+2}$; Lot 2) for Study 34.
[f] MPEG5000-DPPE containing $Ca^{+2}$ (3.04 mg/mL; 980 and 150 ppm $Ca^{+2}$ and $Mg^{+2}$; Lot 1) used in this experiment

TABLE 9

Aqueous phospholipid suspension Microsphere number and Size and acoustic activity.

| Study | Production basis | Microsphere Mean Diameter (microns)[a] N = 2 | Microsphere per mL (×10$^9$)[b] N = 2 | Mean Acoustic (SD) Attenuation[c] (dB/cm/10$^6$ bubbles/mL) |
|---|---|---|---|---|
| 37 | Individual phospholipids with low Ca$^{+2}$ measured in MPEG-5000 DPPE and other components | 1.38, 1.36 | 3.73, 2.92 | 8.9 (0.3) |
| 38 | Phospholipid blend with low Ca$^{+2}$ measured in MPEG-5000 DPPE and other components | 1.34, 1.35 | 3.4, 2.5 | 9.0 (1.3) |

[a]Mean microsphere diameter for microspheres ranging from 1 to 80 microns.
[b]Mean microsphere concentration for microspheres ranging from 1 to 80 microns.
[c]see example methods section for details These studies demonstrate an aqueous phospholipid suspension can be produced using individual phospholipids or a phospholipid blend when the components have a low calcium concentration. Both products have microsphere diameter within the specification of DEFINITY® (see DEFINITY® package insert) and have strong ultrasound acoustic attenuation on a clinical ultrasound machine.

Aspects and Embodiments

Various aspects and embodiments provided by this disclosure are listed below.

Clause 1. A method for preparing a phospholipid suspension, comprising
providing DPPA, DPPC and MPEG5000-DPPE stocks,
measuring calcium concentration of one or more of the DPPC, DPPA and MPEG5000-DPPE stocks,
combining the DPPA, DPPC and/or MPEG5000-DPPE stocks with a non-aqueous solvent to form a phospholipid solution, and
combining the phospholipid solution with an aqueous solvent to form a phospholipid suspension.

Clause 2. The method of clause 1, further comprising measuring calcium concentration of the non-aqueous solvent.

Clause 3. The method of clause 1, wherein the combined measured calcium concentration of the DPPA, DPPC and/or MPEG-DPPE stocks is low.

Clause 4. The method of clause 1 or 3, wherein the combined measured calcium concentration of the DPPA, DPPC and/or MPEG-DPPE stocks and the non-aqueous solvent is low.

Clause 5. The method of clause 1, wherein the calcium concentrations of the DPPC, DPPA and MPEG5000-DPPE stocks are measured.

Clause 6. The method of clause 2, wherein the calcium concentrations of the DPPC, DPPA and MPEG5000-DPPE stocks are measured and the combined measured calcium concentration of the DPPA, DPPC, MPEG-DPPE stocks and the non-aqueous solvent is low.

Clause 7. A method for preparing a phospholipid suspension, comprising
providing DPPA, DPPC and MPEG5000-DPPE stocks,
measuring calcium concentration of one or more of the DPPC, DPPA and MPEG5000-DPPE stocks,
combining DPPA, DPPC and/or MPEG5000-DPPE stocks having a combined measured low calcium concentration with a non-aqueous solvent to form a phospholipid solution, and
combining the phospholipid solution with an aqueous solvent to form a phospholipid suspension.

Clause 8. The method of clause 7, wherein the calcium concentration of the non-aqueous solvent is measured and the DPPA, DPPC, MPEG500-DPPE stocks and the non-aqueous solvent have a combined measured low calcium concentration.

Clause 9. A method for preparing a phospholipid suspension, comprising
combining a MPEG5000-DPPE stock, a DPPA stock, a DPPC stock and a non-aqueous solvent, each with a characterized calcium concentration to form a phospholipid solution, wherein the combined characterized calcium concentration of the MPEG5000-DPPE stock, the DPPA stock, the DPPC stock and the non-aqueous solvent is a low calcium concentration, and
combining the phospholipid solution with an aqueous solvent to form a phospholipid suspension.

Clause 10. A method for preparing a phospholipid suspension, comprising
selecting a MPEG5000-DPPE stock, a DPPA stock and a DPPC stock, one, two or all three of which have a characterized calcium concentration, wherein the combined characterized calcium concentration is a low calcium concentration,
combining said MPEG5000-DPPE stock, DPPA stock, DPPC stock and a non-aqueous solvent to form a phospholipid solution, and
combining the phospholipid solution with an aqueous solvent to form a phospholipid suspension.

Clause 11. A method for preparing a phospholipid suspension, comprising
selecting a MPEG5000-DPPE stock, a DPPA stock and a DPPC stock, each with characterized calcium concentration, wherein the combined characterized calcium concentration is a low calcium concentration,
combining said MPEG5000-DPPE stock, DPPA stock, DPPC stock and a non-aqueous solvent to form a phospholipid solution, and
combining the phospholipid solution with an aqueous solvent to form a phospholipid suspension.

Clause 12. The method of clause 11 wherein the non-aqueous solvent has a characterized calcium concentration, and the combined characterized calcium concentration of the MPEG5000-DPPE, DPPA and DPPC stocks and the non-aqueous solvent is low.

Clause 13. A method for preparing a phospholipid suspension, comprising
measuring calcium concentration of a MPEG5000-DPPE stock,
combining a MPEG5000-DPPE stock having a measured low calcium concentration with a DPPA stock, a DPPC stock, and a non-aqueous solvent to form a phospholipid solution, and
combining the phospholipid solution with an aqueous solvent to form a phospholipid suspension.

Clause 14. The method of clause 11, wherein the non-aqueous solvent comprises (i) propylene glycol or (ii) propylene glycol and glycerol.

Clause 15. The method of clause 13 or 14, wherein the non-aqueous solvent comprises a buffer.

Clause 16. The method of clause 13 or 14, wherein the non-aqueous solvent comprises an acetate buffer.

Clause 17. The method of clause 13 or 14, wherein the aqueous solvent comprises a buffer.

Clause 18. The method of clause 13 or 14, wherein the aqueous solvent comprises a phosphate buffer.

Clause 19. The method of any one of clauses 13-18, wherein the DPPC, DPPA and MPEG5000-DPPE stocks are individually combined with the non-aqueous solvent to form the phospholipid solution.

Clause 20. The method of any one of clauses 13-18, wherein the DPPC, DPPA and MPEG5000-DPPE stocks are sequentially combined with the non-aqueous solvent, in an order-independent manner, to form the phospholipid solution.

Clause 21. The method of any one of clauses 13-18, wherein the DPPC, DPPA and MPEG5000-DPPE stocks are combined with each other to form a phospholipid mixture and the phospholipid mixture is then combined with the non-aqueous solvent to form the phospholipid solution.

Clause 22. The method of any one of clauses 13-18, wherein the DPPC, DPPA and MPEG5000-DPPE stocks are combined with each other to form a phospholipid blend, and the phospholipid blend is combined with the non-aqueous solvent to form the phospholipid solution.

Clause 23. The method of clause 22, wherein the phospholipid blend is formed using an organic solvent dissolution-precipitation process comprising dissolving the DPPC, DPPA and MPEG5000-DPPE stocks into a mixture of methanol and toluene, optionally concentrating the phospholipid/methanol/toluene mixture, and then contacting the concentrated phospholipid/methanol/toluene mixture with methyl t-butyl ether (MTBE) to precipitate the phospholipids to form the phospholipid blend.

Clause 24. The method of any one of clauses 13-23, wherein the low calcium concentration is less than 115 ppm.

Clause 25. The method of any one of clauses 13-24, further comprising placing the phospholipid suspension in a vial and introducing a perfluorocarbon gas into the headspace of the vial.

Clause 26. The method of clause 25, further comprising activating the phospholipid suspension with the perfluorocarbon gas to form an ultrasound contrast agent comprising phospholipid-encapsulated gas microspheres.

Clause 27. The method of clause 26, further comprising administering the ultrasound contrast agent to a subject and obtaining one or more contrast-enhanced ultrasound images of the subject.

Clause 28. The method of any one of clauses 13-27, further comprising measuring calcium concentration of the DPPA stock and/or DPPC stock and/or phospholipid mixture and/or phospholipid blend.

Clause 29. A method for preparing a phospholipid suspension, comprising
measuring calcium concentration of a DPPC stock,
combining a DPPC stock having a measured low calcium concentration with a DPPA stock, a MPEG5000-DPPE stock, and a non-aqueous solvent to form a phospholipid solution, and
combining the phospholipid solution with an aqueous solvent to form a phospholipid suspension.

Clause 30. The method of clause 29, wherein the low calcium concentration is less than 90 ppm.

Clause 31. A method for preparing a phospholipid suspension, comprising
measuring calcium concentration of a DPPA stock,
combining a DPPA stock having a measured low calcium concentration with a DPPC stock, a MPEG5000-DPPE stock, and a non-aqueous solvent to form a phospholipid solution, and
combining the phospholipid solution with an aqueous solvent to form a phospholipid suspension.

Clause 32. The method of clause 31, wherein the low calcium concentration is less than 780 ppm.

Clause 33. A method for preparing a phospholipid suspension, comprising
measuring calcium concentration of a non-aqueous solvent,
combining a non-aqueous solvent having a measured low calcium concentration with a DPPA stock, a DPPC stock, and a MPEG5000-DPPE stock, to form a phospholipid solution, and
combining the phospholipid solution with an aqueous solvent to form a phospholipid suspension.

Clause 34. The method of clause 33, wherein the low calcium concentration is less than 0.7 ppm.

Clause 35. A method for preparing a phospholipid suspension, comprising
selecting a MPEG5000-DPPE stock characterized as having no or low calcium concentration,
combining said MPEG5000-DPPE stock, a DPPA stock, a DPPC stock and a non-aqueous solvent to form a phospholipid solution, and
combining the phospholipid solution with an aqueous solvent to form a phospholipid suspension.

Clause 36. The method of clause 35, wherein the MPEG5000-DPPE stock is further characterized as having no or low divalent metal cation content.

Clause 37. A method for preparing a phospholipid suspension, comprising
combining a MPEG5000-DPPE stock, a DPPA stock, a DPPC stock and a non-aqueous solvent to form a phospholipid solution characterized as having no or low calcium concentration, and
combining the phospholipid solution with an aqueous solvent to form a phospholipid suspension.

Clause 38. A method for imaging a subject comprising
combining a phospholipid suspension with a perfluorocarbon gas to form an ultrasound contrast agent comprising phospholipid-encapsulated gas microspheres,
administering the ultrasound contrast agent to a subject, and
obtaining one or more contrast-enhanced ultrasound contrast images of the subject, wherein the phospholipid suspension is prepared by the method of any one of clauses 1-37.

Clause 39. A method for imaging a subject comprising
combining a phospholipid suspension with a perfluorocarbon gas to form an ultrasound contrast agent comprising phospholipid-encapsulated gas microspheres,
administering the ultrasound contrast agent to a subject, and
obtaining one or more contrast-enhanced ultrasound contrast images of the subject, wherein the phospholipid suspension is prepared by a method comprising
measuring calcium concentration of MPEG5000-DPPE stock,
combining a MPEG5000-DPPE stock having a measured low calcium concentration with a DPPA stock, a DPPC stock, and a non-aqueous solvent to form a phospholipid solution, and
combining the phospholipid solution with an aqueous solvent to form the phospholipid suspension.

Clause 40. A method for imaging a subject comprising
combining a phospholipid suspension with a perfluorocarbon gas to form an ultrasound contrast agent comprising phospholipid-encapsulated gas microspheres,
administering the ultrasound contrast agent to a subject, and obtaining one or more contrast-enhanced ultrasound contrast images of the subject, wherein the phospholipid suspension is prepared by a method comprising selecting a MPEG5000-DPPE stock characterized as having no or low calcium concentration, combining said MPEG5000-DPPE stock, a DPPA stock, a DPPC stock and a non-aqueous solvent to form a phospholipid solution, and combining the phospholipid solution with an aqueous solvent to form a phospholipid suspension.

Clause 41. A method for imaging a subject comprising combining a phospholipid suspension with a perfluorocarbon gas to form an ultrasound contrast agent comprising phospholipid-encapsulated gas microspheres, administering the ultrasound contrast agent to a subject, and obtaining one or more contrast-enhanced ultrasound contrast images of the subject, wherein the phospholipid suspension is prepared by a method comprising combining a MPEG5000-DPPE stock, a DPPA stock, a DPPC stock and a non-aqueous solvent to form a phospholipid solution characterized as having no or low calcium concentration, and combining the phospholipid solution with an aqueous solvent to form a phospholipid suspension.

Clause 42. A method for preparing a phospholipid suspension, comprising individually combining DPPA, DPPC and MPEG5000-DPPE stocks with a propylene glycol (PG)-comprising non-aqueous solvent, in a low or no calcium condition, to form a phospholipid solution, and combining the phospholipid solution with an aqueous solvent to form a phospholipid suspension.

Clause 43. A method for preparing a phospholipid suspension, comprising sequentially combining DPPA, DPPC and MPEG5000-DPPE stocks with a PG-comprising non-aqueous solvent, in a low or no calcium condition, in an order-independent manner, to form a phospholipid solution, and combining the phospholipid solution with an aqueous solvent to form a phospholipid suspension.

Clause 44. A method for preparing a phospholipid suspension, comprising combining, in a methanol and toluene-free condition, DPPA, DPPC and MPEG5000-DPPE stocks to form a phospholipid blend, combining the phospholipid blend with a PG-comprising non-aqueous solvent, in a low or no calcium condition, to form a phospholipid solution, and combining the phospholipid solution with an aqueous solvent to form a phospholipid suspension.

Clause 45. A method for preparing a phospholipid suspension, comprising combining DPPA, DPPC and MPEG5000-DPPE stocks with a blend solvent to form a phospholipid blend, evaporating the blend solvent to form a dried phospholipid blend, combining the dried phospholipid blend with a PG-comprising non-aqueous solvent, in a low or no calcium condition, to form a phospholipid solution, and combining the phospholipid solution with an aqueous solvent to form a phospholipid suspension.

Clause 46. A method for preparing a phospholipid suspension, comprising combining DPPA, DPPC and MPEG5000-DPPE stocks with a blend solvent to form a phospholipid blend, precipitating, in a MTBE-free condition, the phospholipid blend using a second blend solvent, combining the precipitated phospholipid blend with a non-aqueous solvent, in a low or no calcium condition, to form a phospholipid solution, and combining the phospholipid solution with an aqueous solvent to form a phospholipid suspension.

Clause 47. The method of any one of clauses 42-46, wherein the no or low calcium concentration is less than 0.7 ppm.

Clause 48. The method of any one of clauses 42-47, further comprising combining the phospholipid suspension with a perfluorocarbon gas to form an ultrasound contrast agent comprising phospholipid-encapsulated gas microspheres.

Clause 49. The method of clause 48, further comprising administering the ultrasound contrast agent to a subject and obtaining one or more contrast-enhanced ultrasound images of the subject.

Clause 50. A method for imaging a subject comprising combining a phospholipid suspension with a perfluorocarbon gas to form an ultrasound contrast agent comprising phospholipid-encapsulated gas microspheres, administering the ultrasound contrast agent to a subject, and obtaining one or more contrast-enhanced ultrasound contrast images of the subject, wherein the phospholipid suspension is prepared by the method of any one of clauses 42-47.

Clause 51. A composition comprising a phospholipid solution comprising DPPA, DPPC and MPEG5000-DPPE in a non-aqueous solvent and having a low calcium concentration.

Clause 52. A composition comprising a phospholipid solution comprising DPPA, DPPC and MPEG5000-DPPE in a non-aqueous solvent, wherein the DPPA, DPPC and MPEG5000-DPPE and the non-aqueous solvent have a combined characterized calcium ion content that is low.

Clause 53. The composition of clause 51 or 52, wherein the non-aqueous solvent comprises propylene glycol.

Clause 54. The composition of clause 51 or 52, wherein the non-aqueous solvent comprises propylene glycol and glycerol.

Clause 55. The composition of any one of clause 51-54, wherein the non-aqueous solvent comprises a buffer.

Clause 56. The composition of clause 55, wherein the buffer is acetate buffer.

Clause 57. The composition of any one of clauses 51-56, further comprising a perfluorocarbon gas.

Clause 58. The composition of clause 57, wherein the perfluorocarbon gas is perflutren.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of ultrasound contrast imaging a subject comprising
   (a) activating a phospholipid suspension with a perfluorocarbon gas to form lipid-encapsulated gas microspheres, wherein the phospholipid suspension comprises a phospholipid solution having DPPA, DPPC and MPEG5000-DPPE, in a mole % ratio of 10 to 82 to 8 (10:82:8), in propylene glycol, the MPEG5000-DPPE selected as having a calcium concentration of less than 115 parts per million (ppm), and the phospholipid solution having a calcium concentration of less than 0.7 ppm,
   (b) administering the lipid-encapsulated gas microspheres to a subject, and
   (c) obtaining an ultrasound image of the subject.

2. A method of ultrasound contrast imaging a subject comprising
   (a) activating a phospholipid suspension with a perfluorocarbon gas to form lipid-encapsulated gas microspheres, wherein the phospholipid suspension comprises a phospholipid solution made under a methanol and toluene free condition and a methyl t-butyl ether free condition and having DPPA, DPPC and MPEG5000-DPPE, in a mole % ratio of 10 to 82 to 8 (10:82:8), in propylene glycol, the MPEG5000-DPPE having a calcium concentration of less than 115 parts per million (ppm), and the phospholipid solution having a calcium concentration of less than 0.7 ppm,
   (b) administering the lipid-encapsulated gas microspheres to a subject, and
   (c) obtaining an ultrasound image of the subject.

3. The method of claim 2, wherein the calcium concentration is determined using atomic absorption spectroscopy.

4. The method of claim 1, wherein the calcium concentration is determined using atomic absorption spectroscopy.

5. The method of claim 1, wherein the calcium concentration is determined using inductively coupled plasma mass spectrometry (ICP-MS).

6. The method of claim 2, wherein the calcium concentration is determined using inductively coupled plasma-mass spectrometry (ICP-MS).

7. The method of claim 1, wherein the calcium concentration of DPPA is less than 780 ppm, the calcium concentration of DPPC is less than 90 ppm, and the calcium concentration of propylene glycol is less than 0.7 ppm.

8. The method of claim 2, wherein the calcium concentration of DPPA is less than 780 ppm, the calcium concentration of DPPC is less than 90 ppm, and the calcium concentration of propylene glycol is less than 0.7 ppm.

9. The method of claim 2, wherein MPEG5000-DPPE is selected as having a calcium concentration of less than 115 ppm.

\* \* \* \* \*